US008900845B2

(12) United States Patent
Shaw et al.

(10) Patent No.: US 8,900,845 B2
(45) Date of Patent: Dec. 2, 2014

(54) METHODS AND USES OF KSR KINASE, AND MUTATIONS THEREOF

(75) Inventors: Andrey Shaw, St. Louis, MO (US); Jiancheng Hu, St. Louis, MO (US); Haiyang Yu, St. Louis, MO (US)

(73) Assignee: Washington University, Saint Louis, MO (US)

( * ) Notice: Subject to any disclaimer, the term of this patent is extended or adjusted under 35 U.S.C. 154(b) by 141 days.

(21) Appl. No.: 13/369,220

(22) Filed: Feb. 8, 2012

(65) Prior Publication Data
US 2012/0202233 A1 Aug. 9, 2012

Related U.S. Application Data

(60) Provisional application No. 61/462,797, filed on Feb. 8, 2011.

(51) Int. Cl.
*C12N 9/12* (2006.01)
*C12N 9/02* (2006.01)

(52) U.S. Cl.
CPC ............ *C12N 9/0069* (2013.01); *C12N 9/1205* (2013.01); *C07K 2319/70* (2013.01); *G01N 2333/90241* (2013.01); *G01N 2333/9121* (2013.01)
USPC .......................................................... 435/194

(58) Field of Classification Search
None
See application file for complete search history.

(56) References Cited

U.S. PATENT DOCUMENTS

| 7,592,142 B2 | 9/2009 | Druker et al. |
| 2009/0047675 A1 | 2/2009 | Roberts et al. |
| 2010/0209488 A1 | 8/2010 | Wrasidlo et al. |

FOREIGN PATENT DOCUMENTS

| WO | 2005/056756 | 6/2005 |
| WO | 2010/141062 | 12/2010 |

OTHER PUBLICATIONS

NCBI protein search "Kinase Suppressor of RAS mouse". Performed May 19, 2014.*
Baas, A.F., et al., "Activation of the tumour suppressor kinase LKB1 by the STE20-like pseudokinase STRAD" EMBO J. 22: 3062-3072, 2003.
Barouch-Bentov, R., et al., "A Conserved Salt Bridge in the G-Loop of Multiple Protein Kinases is Important for Catalysis and for in Vivo Lyn Function", Mol. Cell. 33: 43-52. 2009.
Bártová, I., et al., "Activation and inhibition of cyclin-dependent kinase-2 by phosphorylation; a molecular dynamics study reveals the functional importance of the glycinerich loop," Protein Science 13:1449-1457, 2004.
Brose, M. S. et al., BRAF and RAS mutations in human lung cancer and melanoma, Cancer Res. 62, 6997-7000, 2002.
Channavajhala, P.L., et al., Identification of a novel human kinase supporter of Ras (hKSR-2) that functions as a negative regulator of Cot (TpI2) signaling, J. Biol. Chem. 278, 47089-47097, 2003.
Dhomen, N., et al., New insight into BRAF mutations in cancer, Curr. Opin. Genet. Dev. 17, 31-39, 2007.
Fusello, A.M., et al., The MAPK scaffold kinase suppressor of Ras is involved in ERK activation by stress and proinflammatory cytokines and induction of arthritis, J. Immunol. 177, 6152-6158, 2006.
Garnett, M.J., et al., Wild-type and mutant B-RAF activate C-RAF through distinct mechanisms involving heterodimerization, Mol. Cell 20, 963-969, 2005.
Gibbs, C.S., et al., Systematic mutational analysis of cAMP-dependent protein kinase identifies unregulated catalytic subunits and defines regions important for the recognition of the regulatory subunit, J. Biol. Chem. 267, 4806-4814, 1992.
Hatzivassiliou, G., et al., RAF inhibitors prime wild-type RAF to activate the MAPK pathway and enhance growth, Nature 464, 431-435, 2010.
Heidorn, S. J., et al., Kinase-dead BRAF and oncogenic RAS cooperate to drive tumor progression through CRAF, Cell 140, 209-221, 2010.
Iyer, G.H., et al., Catalytic independent functions of a protein kinase as revealed by a kinase-dead mutant: study of the Lys72His mutant of cAMP-dependent kinase, J. Mol. Biol. 351, 1110-1122, 2005.
Iwashita, T., et al., "Biological and biochemical properties of Ret with kinase domain mutations identified in multiple endocrine neoplasia type 2B and familial medullary thyroid carcinoma" Oncogene 18: 3919-3922, 1999.
Kolesnick, R., et al., Inflammatory bowel disease reveals the kinase activity of KSR1, J. Clin. Invest. 114, 1233-1237, 2004.
Kornfeld, K., et al., The ksr-1 gene encodes a novel protein kinase involved in Ras-mediated signaling in *C. elegans*, Cell 83, 903-913, 1995.
McKay, M. M., et al., Signaling dynamics of the KSR1 scaffold complex, Proc. Natl. Acad. Sci. USA 106, 11022-11027, 2009.
Michaud, N. R., et al., KSR stimulates Raf-1 activity in a kinase-independent manner, Proc. Natl. Acad. Sci. USA 94, 12792-12796, 1997.
Morrison, D. K., KSR: a MAPK scaffold of the Ras pathway?, J. Cell Sci. 114, 1609-1612, 2001.
Nazarian, R., et al., Melanomas acquire resistance to B-RAF(V600E) inhibition by RTK or N-RAS upregulation, Nature 468, 973-977, 2010.
Nguyen, A., et al., Kinase suppressor of Ras (KSR) is a scaffold which facilitates mitogen-activated protein kinase activation in vivo, Mol. Cell Biol. 22, 3035-3045, 2002.
Niault, T.S., et al., Targets of Raf in tumorigenesis, Carcinogenesis 31, 1165-1174, 2010.
Paulmurugan, R., et al., Molecular Imaging of Drug-Modulated Protein-Protein Interactions in Living Subjects, Cancer Res 64, 2113-2119, 2004.
Poulikakos, P. I., et al., RAF inhibitors transactivate RAF dimers and ERK signalling in cells with wild-type BRAF, Nature 464, 427-430, 2010.
Rajakulendran, T., et al., A dimerization-dependent mechanism drives RAF catalytic activation, Nature 461, 542-545, 2009.
Stewart, S., et al Kinase suppressor of Ras forms a multiprotein signaling complex and modulates MEK localization, Mol. Cell Biol. 19, 5523-5534, 1999.

(Continued)

*Primary Examiner* — Sheridan Swope
(74) *Attorney, Agent, or Firm* — Zackson Law LLC; Saul L. Zackson

(57) ABSTRACT

Mutant KSR proteins are disclosed. The mutants include single amino acid substitutions, leading to either a loss of kinase activity or a loss of scaffolding activity. Also disclosed are methods of screening compounds for inhibitors of KSR kinase activity or KSR scaffolding activity. In some embodiments, the screening methods include protein complementation assays in which nucleic acids encoding fusion constructs comprising enzyme portions and kinase dimerization domains are expressed in cells. Inhibitors of dimerization can be indicated by loss of enzyme activity.

2 Claims, 4 Drawing Sheets

(56) References Cited

OTHER PUBLICATIONS

Sundaram, M., et al., The *C. elegans* ksr-1 gene encodes a novel Raf-related kinase involved in Ras-mediated signal transduction, Cell 83, 889-901, 1995.

Taylor, S.S. et al., Protein kinases: evolution of dynamic regulatory proteins, Trends Biochem. Sci., 2010.

Taylor, S.S. et al., Yet another "active" pseudokinase, Erb3, Proc. Nat'l. Acad. Sci. USA 107, 8047-8048, 2010.

Therrien, M., et al., A genetic screen for modifiers of a kinase suppressor of Ras-dependent rough eye phenotype in *Drosophila*, Genetics 156, 1231-1242, 2000.

Therrien, M., et al., KSR modulates signal propagation within the MAPK cascade, Genes Dev. 10, 2684-2695, 1996.

Therrien, M., et al., KSR, a novel protein kinase required for RAS signal transduction, Cell 83, 879-888, 1995.

Tsai, J., et al., Discovery of a selective inhibitor of oncogenic B-Raf kinase with potent antimelanoma activity, Proc. Natl. Acad. Sci. U S A 105, 3041-3046, 2008.

Wan, P.T., et al. Mechanism of activation of the RAF-ERK signaling pathway by oncogenic mutations of B-RAF, Cell 116, 855-867, 2004.

Xing, H.R., et al., Kinase suppressor of Ras signals through Thr269 of c-Raf-1, J. Biol. Chem. 276, 9733-9741, 2001.

Xing, H.R., et al., The kinase activity of kinase suppressor of Ras1 (KSR1) is independent of bound MEK, J. Biol. Chem. 279, 26210-26214, 2004.

Zafrullah, M., et al., Kinase suppressor of Ras transphosphorylates c-Raf-1, Biochem. Biophys. Res. Commun. 390, 434-440, 2009.

\* cited by examiner

FIG.3
A  B-RAF:Sorafenib
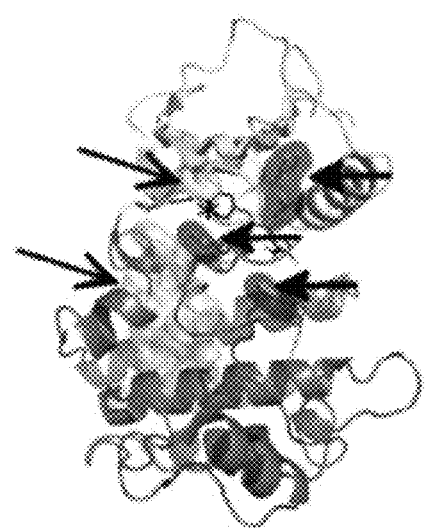
B  C-RAF:GDC
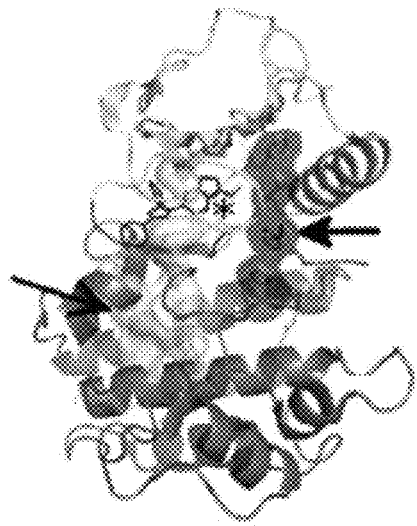
C
B-RAF+Sorafenib    C-RAF+GDC    C-RAF A373F model

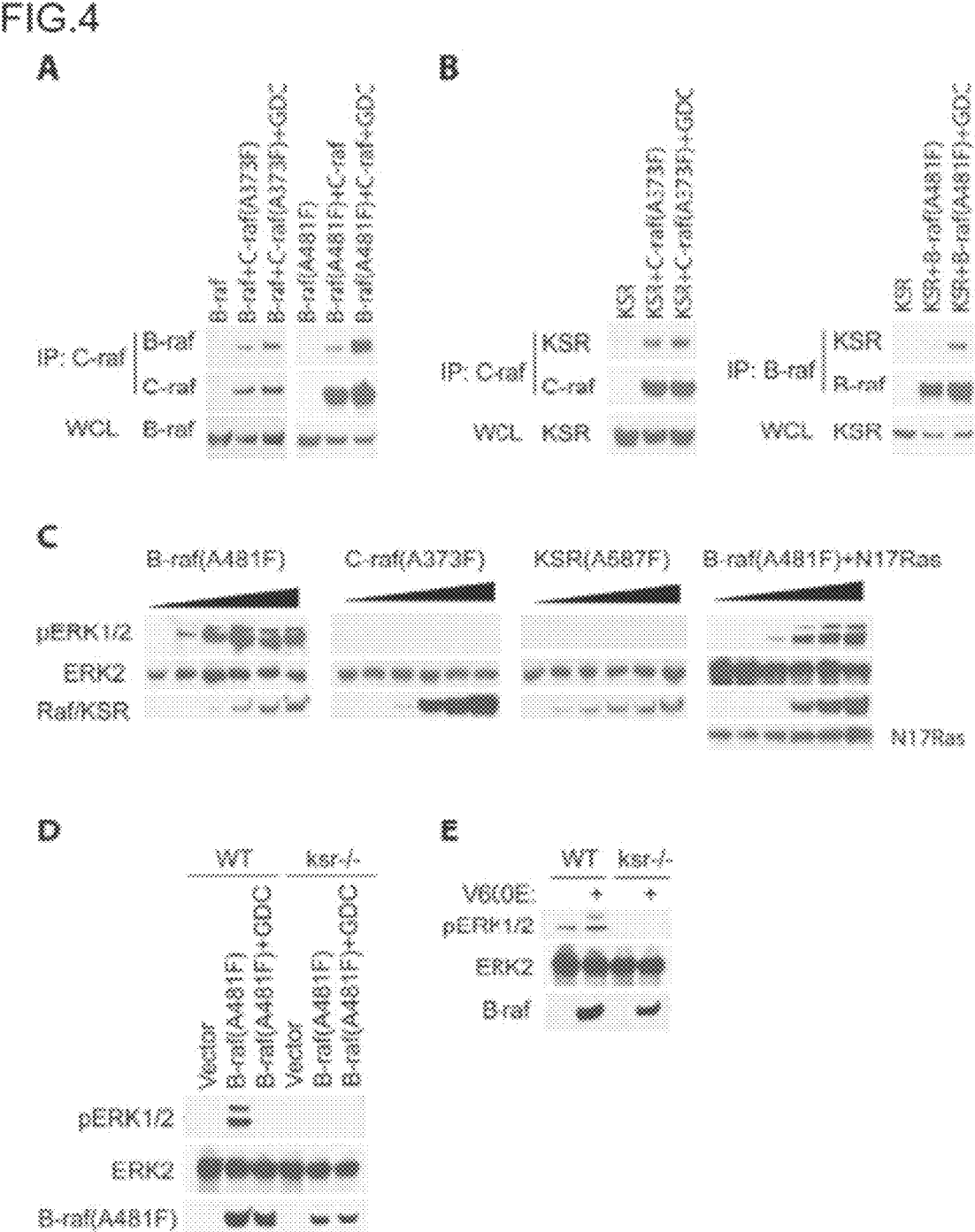

METHODS AND USES OF KSR KINASE, AND MUTATIONS THEREOF

CROSS-REFERENCE TO RELATED APPLICATIONS

The present application is a U.S. Non-Provisional claiming priority to U.S. Provisional Patent Application Ser. No. 61/462,797 filed Feb. 8, 2011, which is herein incorporated by reference in its entirety.

INCORPORATION BY REFERENCE OF SEQUENCE LISTING

The Sequence Listing, which is a part of the present disclosure, includes a computer readable form and a written sequence listing comprising nucleotide and/or amino acid sequences. The sequence listing information recorded in computer readable form is identical to the written sequence listing. The subject matter of the Sequence Listing is incorporated herein by reference in its entirety.

INTRODUCTION

Mutations in RAS and BRAF represent the majority of oncogenic mutations in most human cancers including malignant melanoma (Brose, M. S. et al., Cancer Res. 62, 6997-7000, 2002). While BRAF-specific inhibitors have shown promise in the clinic, some of them have a paradoxical effect, inhibiting cells with mutated BRAF but accelerating the growth of cells with mutated RAS (Hatzivassiliou, G., et al., Nature 464, 431-435, 2010; Heidorn, S. J., et al., Cell 140, 209-221, 2010; Poulikakos, P. I., et al., Nature 464, 427-430; 2010) About 40% of human melanomas comprise a constitutively active mutation of BRAF, i.e., BRAF V600E. Recent studies suggest that in RAS transformed cells, these BRAF-specific inhibitors can bind to and induce the closed, active conformation of the wild-type forms of BRAF and CRAF RAS (Hatzivassiliou, G., et al., Nature 464, 431-435, 2010; Tsai, J., et al., Proc. Natl. Acad. Sci. USA 105, 3041-3046, 2008). This allows dimers between BRAF and CRAF to form, and through a mechanism that is unknown, dimerization results in the activation of CRAF and downstream signaling pathways.

Interestingly, one of the drugs tested, PLX4720, induces MEK activation in RAS transformed cells and also induces the closed, active conformation of BRAF but does not induce BRAF/CRAF dimers (Hatzivassiliou, G., et al., Nature 464, 431-435, 2010; Poulikakos, P. I., et al., Nature 464, 427-430, 2010; Tsai, J., et al., Proc. Nat'l. Acad. Sci. USA 105, 3041-3046, 2008). These findings suggest that the mechanism of activation might not be related to BRAF/CRAF dimers but to other proteins that bind to the closed active conformation of BRAF and CRAF. The scaffold protein Kinase Suppressor of RAS (KSR) can form dimers with both RAF isoforms (McKay, M. M., et al., Proc. Natl. Acad. Sci. USA 106, 11022-11027, 2009; Rajakulendran, T., et al., Nature 461, 542-545, 2009).

KSR was first discovered in *Drosophila* and *C. elegans* as a positive effector of the RAS/MAP kinase signaling pathway (Kornfeld, K., et al., Cell 83, 903-913, 1995; Sundaram, M., et al., Cell 83, 889-901, 1995; Therrien, M., et al., Cell 83, 879-888, 1995). Genetic epistasis experiments place KSR in a position either upstream or parallel with RAF. While KSR is closely related to RAF, the absence of the critical catalytic lysine (in mammalian forms of KSR) and the lack of any convincing evidence for in vitro kinase activity (Michaud, N. R., et al., Proc. Natl. Acad. Sci. USA 94, 12792-12796, 1997) has led to the model that KSR functions mainly as a non-catalytic scaffold for the RAS/MAP kinase signaling pathway. KSR forms stable complexes with RAF and MEK, suggesting that it may function to facilitate MEK phosphorylation by RAF. A recent paper from the Morrison group suggests that BRAF, MEK and KSR form a ternary complex mediated by MEK bound to KSR and an N-terminal domain (CA1) of KSR (McKay, M. M., et al., Proc. Natl. Acad. Sci. USA 106, 11022-11027, 2009). Based on the asymmetric packing of RAF molecules in the crystal structures, Therrien's group suggested that a side-to-side dimer interface, conserved in KSR and in all isoforms of RAF, mediates the ability of RAF to form dimers with itself or with KSR (Rajakulendran, T., et al., Nature 461, 542-545, 2009). BRAF appears to activate CRAF via dimerization and without requiring kinase activity (Hatzivassiliou, G., et al., Nature 464, 431-435, 2010; Heidorn, S. J., et al., Cell 140, 209-221, 2010; Poulikakos, P. I., et al., Nature 464, 427-430, 2010).

Understanding how the MAP kinase signaling complex functions has been particularly challenging given there are at least three kinases in the cascade and an even larger number of components identified by genetic epistasis whose function is still unknown (Rubin, G. M., et al. Cold Spring Harb. Symp. Quant. Biol. 62, 347-352, 1997; Therrien, M., et al., Genetics 156, 1231-1242, 2000). While the canonical pathway involving RAS, RAF, MEK and ERK has been known for over a decade, important details about the mechanism of activation are still unknown especially regarding the role of KSR and the function of the different RAF isoforms.

Recent data suggest that the roles of the three RAF isoforms, ARAF, BRAF and CRAF are more complex than initially thought (Dhomen, N., et al., Curr. Opin. Genet. Dev. 17, 31-39, 2007). BRAF and CRAF are widely expressed, and are expressed together in most cells, while ARAF expression is restricted mainly to germ cells (Niault, T. S., et al., Carcinogenesis 31, 1165-1174, 2010). Originally, each RAF isoform was thought to phosphorylate MEK independently. Recent studies, however suggest that the RAF isoforms have a hierarchy, with BRAF able to activate CRAF but not the other way around (Wan, P. T., et al. Cell 116, 855-867, 2004; Garnett, M. J., et al., Mol. Cell 20, 963-969, 2005). By a mechanism that does not require kinase activity, dimerization of BRAF with CRAF induces the activation of CRAF3 (Wan, P. T., et al. Cell 116, 855-867, 2004; Garnett, M. J., et al., Mol. Cell 20, 963-969, 2005). This is supported by the finding that oncogenic forms of BRAF that lack kinase activity can still drive activation of the pathway (Heidorn, S. J., et al., Cell 140, 209-221, 2010). The function of these catalytically impaired mutants requires RAS presumably to induce the active conformation of BRAF and also the presence of a catalytically active CRAF molecule to convey the signal downstream. The mechanism of CRAF activation is not known but could be either through an allosteric interaction or by the recruitment of accessory proteins that are associated with BRAF (or KSR) to modify and activate CRAF. In contrast, oncogenic forms of BRAF that have enhanced kinase activity like the V600E mutant are both CRAF and RAS independent (Garnett, M. J., et al., Mol. Cell 20, 963-969, 2005) suggesting that they directly phosphorylate and activate MEK.

Because genetic and biochemical proof for KSR kinase activity has been lacking, KSR has been considered to be a pseudokinase that scaffolds the MAP kinase pathway by binding to RAF, MEK and ERK. Because mutagenesis strategies that impair catalytic activity result in dynamic structures that have impaired scaffold activity, it is difficult to distinguish between the two functions of kinases using traditional mutagenesis approaches.

SUMMARY

Some embodiments of the present teachings include a mutant of KSR that impairs the ability of KSR to bind to ATP and does not reconstitute KSR function. The inventors have found that ATP binding can be required for KSR activity. The inventors have found that activity of the BRAFV600E mutant, found in about 60% of melanoma tumor requires the presence of KSR. The inventors further disclose that the ATP binding site of KSR can be a target for a pharmaceutical compound that can be used to treat diseases such as cancers, including, without limitation, melanoma.

The present inventors have found that a mechanism for RAF activation can include drug induced dimer formation between CRAF and KSR. The inventors further found that in some embodiments, both CRAF and KSR can be required but that BRAF expression can be dispensable for the effect.

The present inventors have found that a mechanism for RAF activation can involve induced complex formation between CRAF and KSR. The present inventors disclose that inhibition of CRAF/KSR dimers can inhibit RAF and RAS activation.

The present inventors have generated mutants, including mutants of kinases and mutants of KSR. In various embodiments, these mutants do not bind ATP. In various embodiments, these mutants can comprise a closed, active conformation of a kinase or a related protein, such as, without limitation, KSR. In some configurations, a mutation can comprise an alanine-to-phenylalanine mutation in the sequence of the KSR polypeptide chain. The present teachings further include alanine-to-phenylalanine mutations at highly conserved homologous sequences not only in KSR, but also in kinases other than KSR, such as BRAF and CRAF. In various aspects, such mutant kinases also do not bind ATP. In various embodiments, these alanine-to-phenylalanine mutations can also comprise a closed, active conformation. A conception of the present inventors includes any kinase and homologous polypeptide comprising an alanine-to-phenylalanine mutation at a homologous sequence which can be a conserved sequence.

In some embodiment, the present teachings include methods of identifying or designing a compound that can act as an inhibitor of KSR kinase activation. In some configurations, a compound identified by these methods can be used as a cancer therapeutic. In these methods, interacting surfaces of kinase dimers, including KSR/KSR homodimer, KSR/CRAF heterodime, KSR/BRAF heterodimer, BRAF/BRAF homodimer, BRAF/CRAF heterdimer, or CRAF/CRAF homodimer (collectively, KSR/CRAF/BRAF) and models thereof can be used to design inhibitors.

In some configurations, interaction between an N-terminal sequence of one kinase (residues Y340/W342 in CRAF, D448/W450 in BRAF) which interact with R506/K507 of the alpha-C helix of BRAF or residues R398/K399 of the alpha-C helix in CRAF can be a target for drug design. While D448 of BRAF allows BRAF to activate either BRAF or CRAF constitutively, CRAF requires phosphorylation of Y340 to allow it to phosphorylate CRAF or BRAF. Since KSR lacks an acidic residue in the position corresponding to Y340 in CRAF or D448 in BRAF, KSR can only be activated by BRAF or CRAF but cannot activate BRAF or CRAF. The activation of RAF is in trans and involves acidic residues in the activating partner. In some embodiments, the present teachings include an oligopeptide of sequence MKTLGRRDDDDDWEIP-DGGI (SEQ ID NO: 9). This oligopeptide was designed based on structures involved in interaction, in particular the N-terminal activating sequence of BRAF (mktlgrrdssddweipdgq; SEQ ID NO: 10). This oligopeptide can inhibit CRAF kinase activity. In other configurations, an inhibitor identified by these methods can be, without limitation, a small molecule, a peptide, an antibody, or an antigen-binding fragment of an antibody such as a Fab fragment. An antibody of the present teachings can be a polyclonal or a monoclonal antibody.

The present inventors also used molecular modeling which indicated that in various configurations, an alanine-to-phenylalanine mutant of KSR can comprise two stabilized hydrophobic spines. Without being limited by theory, the inventors further hypothesize that the stabilized hydrophobic spines can be critical for a closed active conformation.

A conception of the present inventors includes any kinase comprising the alanine-to-phenylalanine mutation at the homologous sequence, as well as multimers, such as heterodimers and homodimers comprising a polypeptide comprising the alanine-to-phenylalanine mutation. In various embodiments, a conception of the present inventors includes polypeptides homologous to kinases that comprise the alanine-to-phenylalanine mutation at the homologous sequence, as well as multimers, such as heterodimers and homodimers comprising a polypeptide comprising the alanine-to-phenylalanine mutation. Other aspects of the present teachings include nucleic acids encoding mutations comprising the conserved alanine-to-phenylalanine mutation of KSR, as well as nucleic acids encoding other kinases, or homologues thereof, wherein the kinases or homologues thereof comprise an alanine-to-phenylalanine mutant homologous to A587F of KSR (with amino acid numbering in reference to the sequence of Mus musculus KSR). In various configuration, the nucleic acid can be a DNA or an RNA, and can encode, for example, BRAF A481 F or CRAF A373F.

In some embodiments, the present teachings include methods to discriminate between scaffold versus kinase functions of KSR. The inventors found that the alanine-to-phenylalanine mutant of KSR can bind constitutively to RAF and MEK but cannot reconstitute activity. Without being limited by theory, this can imply that the catalytic activity of KSR can be required for its function.

The present inventors further disclose that two different inhibitors (PLX4720 and GDC0879, Selleck Chemicals, Houston, Tex.) can induce CRAF/KSR dimers. The inventors further disclose that the ability of BRAF-specific inhibitors to activate MEK and ERK in RAS transformed cells require KSR.

The present inventors generated a mutated form of KSR. In some configurations, this mutated form can dimerize constitutively with CRAF but cannot hind ATP. Without being limited by theory, the failure of this mutant to reconstitute KSR function suggested to the present inventors that the scaffolding function of KSR with CRAF might not be sufficient for its function. The present inventors further disclose that while KSR exhibits no kinase activity when expressed alone, co-expression and dimerization of KSR with CRAF can result in detectable KSR kinase activity for MEK. The inventors further determined that KSR can be a bona fide kinase whose activity can be required for activation of MEK.

The present inventors have determined that KSR can be a target for a drug for treating a cancer, such as a tumor in which the cells are resistant to BRAF inhibitors such as PLX4032. Furthermore, the inventors have determined that because KSR, CRAF and BRAF can form homodimers and heterodimers, that the interacting surfaces of these polypeptides can be used to identify or design an inhibitor of kinase activation and/or protein scaffolding. The present teachings include the application of structure-based identification of inhibitors that can disrupt a KSR/KSR homodimer interface, a KSR/BRAF heterodimer interface, a KSR/CRAF heterodimer interface, a BRAF/BRAF homodimer interface, a BRAF/CRAF heterodimer interface, or a CRAF/CRAF homodimer interface.

In various embodiments, the methods developed by the present inventors can involve multilevel investigations, such as analysis of three-dimensional structures and models of kinase homodimer and heterodimer complexes, and various analytical tools, including virtual docking of chemical databases to kinase dimerization domains and in silico screening of chemical structures as potential inhibitors; tests of candidate compounds for inhibitory effects on kinase activity, tests for specificity of candidate compounds, and/or tests to investigate the effects of a candidate inhibitor on dimerization or kinase activity. In various configurations, compounds identified can be, without limitation, a small molecule, an oligopeptide, an aptamer.

In some aspects, methods of the present teachings can include identifying the binding site involved in hetero- or homo-dimerization, in a computer-based model of kinase dimers. To identify candidate inhibitors, these sites can be targeted by docking and scoring of compounds comprised by one or more libraries of virtual compounds. High scoring candidate compounds can be purchased and/or synthesized. A candidate compound can be tested for its ability to inhibit tumor growth in vitro or in vivo, its ability to inhibit kinase activity of a polypeptide comprising a target sequence, and/or is ability to inhibit dimerization, for example through a chemical cross-linking assay of dimer formation.

In some aspects, the present inventors have developed methods for designing a drug which inhibits activity of KSR. In various configurations, these methods comprise providing on a digital computer a three-dimensional structure of a KSR/CRAF/BRAF homodimer or heterodimer complex; using software comprised by the digital computer to design a chemical compound which is predicted to bind to a homodimer or heterodimer, and in particular to the interface between binding domains in a dimer. In some aspects, the methods can involve virtual screening not only of an actual 3-dimensional structure of a dimer developed using x-ray crystallography, but also virtual screening of a homology model, whereby candidate inhibitory compounds can be identified using conceptual structures of homodimerized and/or heterodimerized domains of a KSR/C RAF/BRAF homodimer or heterodimer.

Also disclosed herein are methods for testing a compound as a KSR/CRAF/BRAF inhibitor in a cell or tissue. These methods comprise: selecting a candidate inhibitor of KSR/CRAF/BRAF dimerization and/or kinase activity by performing a structure-based drug design using a three-dimensional structure determined for a crystal comprising an KSR/CRAF/BRAF dimer; contacting the cell or tissue with the candidate inhibitor; and determining a change of an activity of the KSR/CRAF/BRAF dimer comprised by the cell or tissue.

In yet other aspects, the present teachings include methods for decreasing KSR/CRAF/BRAF dimer activity such as KSR activity in a subject for the treatment of a disease such as a cancer. These methods can comprise selecting a compound identified as an inhibitor of KSR/CRAF/BRAF dimerization using a three-dimensional structure determined for a crystal comprising a KSR/CRAF/BRAF dimer, and administering a therapeutically effective amount of the inhibitor to a subject in need thereof. A disease of these aspects can be, without limitation, a cancer, a cancer such as a cancer of the breast, a cancer of the ovary or the uterus, or a melanoma.

In yet other aspects, the present teachings include compounds identified by the screening methods set forth herein, as well as salts thereof such as pharmaceutically acceptable salts. In some configurations, the present teachings include stereoisomers of the compounds, and salts thereof. The compounds can function as inhibitors of KSR/CRAF/BRAF dimerization, such as KSR/BRAF dimerization, and can be used in therapeutic applications such as oncology (such as, for example, breast, ovarian, uterine cancers or melanomas) and/or in a research context.

In some aspects, a screening method of the present teachings can include a "top-down" approach to identifying lead compounds which inhibit KSR/CRAF/BRAF dimerization.

First, on level 1, candidate compounds can be selected. Selection of these compounds can comprise virtual docking of a chemical database to a KSR/CRAF/BRAF dimerization "hot-spot." Level 2 can comprise testing the candidate compounds for activity as inhibitors of KSR/CRAF/BRAF activation. These methods can comprise assays for KSR/CRAF/BRAF activity that are well known to skilled artisans, such as, for example, Western blot assays on kinase autophosphorylation or phosphorylation of a downstream target such as MEK kinase. In level 3, compounds can be tested for selectivity using methods well known to skilled artisans, such as, for example, Western blot assays for effects of a compound on related kinases. In level 4, further analysis of a candidate compound can comprise investigations into mechanism, such as, in non-limiting example, split-luciferase assays, cross-linking assays, and kinase binding assays. In level 5, lead candidate compounds can be optimized. This optimization can comprise performing a structural similarity search for related compounds in at least one additional database, which can be, for example a larger database. The optimization level analysis can also comprise synthesis of a focused combichem library. Because the last level can suggest new compounds to test, in some configurations, these new compounds can be taken through the levels in a new cycle of analysis.

A KSR of the present teachings can be a mammalian KSR. A KSR of the present teachings can be a human KSR. A KSR (wild type) of the present teachings can have an amino acid sequence as set forth in SEQ ID NO: 1.

```
                                                                    (SEQ ID NO: 1)
  1 mneakvketl rrcgasgdec grlqyaltcl rkvtglggeh kedsswssld arresgsgps 61 tdtlsaaslp wppgssqlgr agnsaqgprs isvsalpasd sptpsfsegl sdtciplhas 121 grltpralhs fitppttpql rrhtklkppr tppppsrkvf qllpsfptlt rskshesqlg 181 nriddvssmr fdlshgspqm vrrdiglsvt hrfstkswls qvchvcqksm ifgvkckhcr 241 lkchnkctke apacrisflp ltrlrrtesv psdinnpvdr aaephigtlp kaltkkehpp
```

-continued

```
301 amnhldsssn pssttsstps spapfptssn pssattppnp spgqrdsrfn fpaayfihhr
361 qqfifpvpsa ghcwkcllia eslkenafni safahaaplp eaadgtrldd qpkadvleah
421 eaeaeepeag kseaeddede vddlpssrrp wrgpisrkas qtsvylqewd ipfeqvelge
481 pigqgrwgrv hrgrwhgeva irllemdghn qdhlklfkke vmnyrqtrhe nvvlfmgacm
541 npphlaiits fckgrtlhsf vrdpktsldi nktrqiaqei ikgmgylhak givhkdlksk
601 nvfydngkvv itdfglfgis gvvregrren qlkishdwlc ylapeivrem tpgkdedqlp
661 fskaadvyaf gtvwyelqar dwplknqaae asiwqigsge gmkrvltsys lgkevseils
721 acwafdlqer psfsllmdml eklpklnrrl shpghfwksa el.
```
(NCBI Accession NP_055053.1).

A human KSR mutant including A587F of the present teachings can have amino acid sequence

```
                                                              (SEQ ID NO: 2)
  1 mneakvketl rrcgasgdec grlqyaltcl rkvtglggeh kedsswssld arresgsgps
 61 tdtlsaaslp wppgssqlgr agnsaqgprs isvsalpasd sptpsfsegl sdtciplhas
121 grltpralhs fitppttpql rrhtklkppr tppppsrkvf qllpsfptlt rskshesqlg
181 nriddvssmr fdlshgspqm vrrdiglsvt hrfstkswls qvchvcqksm ifgvkckhcr
241 lkchnkctke apacrisflp ltrlrrtesv psdinnpvdr aaephfgtlp kaltkkehpp
301 amnhldsssn pssttsstps spapfptssn pssattppnp spgqrdsrfn fpaayfihhr
361 qqfifpvpsa ghcwkcllia eslkenafni safahaaplp eaadgtrldd qpkadvleah
421 eaeaeepeag kseaeddede vddlpssrrp wrgpisrkas qtsvylqewd ipfeqvelge
481 pigqgrwgrv hrgrwhgevf irllemdghn qdhlklfkke vmnyrqtrhe nvvlfmgacm
541 npphlaiits fckgrtlhsf vrdpktsldi nktrqiaqei ikgmgylhak givhkdlksk
601 nvfydngkvv itdfglfgis gvvregrren qlkishdwlc ylapeivrem tpgkdedqlp
661 fskaadvyaf gtvwyelqar dwplknqaae asiwqigsge gmkrvltsvs lgkevseils
721 acwafdlqer psfsllmdml eklpklnrrl shpghfwksa el.
```

BRAF (wild type) of the present teachings can have amino acid sequence

```
                                                              (SEQ ID NO: 3)
  1 maalsggggg gaepgqalfn gdmepeagag agaaassaad paipeevwni kqmikltqeh
 61 iealldkfgg ehnppsiyle ayeeytskld alqqreqqll eslgngtdfs vsssasmdtv
121 tsssssslsv lpsslsvfqn ptdvarsnpk spqkpivrvf lpnkqrtvvp arcgvtvrds
181 lkkalmmrgl ipeccavyri qdgekkpigw dtdiswltge elhvevlenv pltthnfvrk
241 tfftlafcdf crkllfqgfr cqtcgyklhq rcstevplmc vnydqldllf vskffehhpi
301 pqeeaslaet altsgsspsa pasdsigpqi ltspspsksi pipqpfrpad edhrnqfgqr
361 drsssapnvh intiepvnid dlirdqgfrg dggsttglsa tppaslpgsl tnvkalqksp
421 gpqrerksss ssedrnrmkt lgrrdssddw eipdgqitvg qrigsgsfgt vykgkwhgdv
481 avkmlnvtap tpqqlqafkn evgvlrktrh vnillfmgys tkpqlaivtq wcegsslyhh
541 lhiietkfem iklidiarqt aqgmdylhak siihrdlksn niflhedltv kigdfglatv
601 ksrwsgshqf eqlsgsilwm apevirmqdk npysfqsdvy afgivlyelm tgqlpysnin
661 nrdqiifmvg rgylspdlsk vrsncpkamk rlmaeclkkk rderplfpqi lasiellars
```

```
721 lpkihrsase pslnragfqt edfslyacas pktpiqaggy gafpvh
```
(Swiss-Prot Accession P15056.4).

BRAF A481 F, comprising an alanine-to-phenylalanine mutation as described herein which is homologous to KSR A587F can have an amino acid sequence

```
                                                       (SEQ ID NO: 4)
  1 maalsggggg gaepgqalfn gdmepeagag agaaassaad paipeevwni kqmikltqeh
 61 iealldkfgg ehnppsiyle ayeeytskld alqqreqqll eslgngtdfs vsssasmdtv
121 tssssssslsv lpsslsvfqn ptdvarsnpk spqkpivrvf lpnkqrtvvp arcgvtvrds
181 lkkalmmrgl ipeccavyri qdgekkpigw dtdiswltge elhvevlenv pltthnfvrk
241 tfftlafcdf crkllfqgfr cqtcgykfhq rcstevplmc vnydqldllf vskffehhpi
301 pqeeaslaet altsgsspsa pasdsigpqi ltspspsksi pipqpfrpad edhrnqfgqr
361 drsssapnvh intiepvnid dlirdqgfrg dggsttglsa tppaslpgsl tnvkalqksp
421 gpqrerksss ssedrnrmkt lgrrdssddw eipdgqitvg qrigsgsfgt vykgkwhgdv
481 fvkmlnvtap tpqqlqafkn evgvlrktrh vnillfmgys tkpqlaivtq wcegsslyhh
541 lhiietkfem iklidiarqt aqgmdylhak siihrdlksn niflhedltv kigdfglatv
601 ksrwsgshqf eqlsgsilwm apevirmqdk npysfqsdvy afgivlyelm tgqlpysnin
661 nrdqiifmvg rgylspdlsk vrsncpkamk rlmaeclkkk rderplfpqi lasiellars
721 lpkihrsase pslnragfqt edfslyacas pktpiqaggy gafpvh.
```

CRAF (wild type) of the present teachings can have amino acid sequence

```
                                                       (SEQ ID NO: 5)
  1 mehiqgawkt isngfgfkda vfdgsscisp tivqqfgyqr rasddgkltd psktsntirv
 61 flpnkqrtvv nvrngmslhd clmkalkvrg lqpeccavfr llhehkgkka rldwntdaas
121 ligeelqvdf ldhvpltthn farktflkla fcdicqkfll ngfrcqtcgy kfhehcstkv
181 ptmcvdwsni rqlllfpnst igdsgvpalp sltmrrmres vsrmpvssqh rystphaftf
241 ntsspssegs lsqrqrstst pnvhmvsttl pvdsrmieda irshsesasp salsssspnnl
301 sptgwsqpkt pvpaqrerap vsgtqeknki rprgqrdssy yweieasevm lstrigsgsf
361 gtvykgkwhg dvavkilkvv dptpeqfqaf rnevavlrkt rhvnillfmg ymtkdnlaiv
421 tqwcegssly khlhvqetkf qmfqlidiar qtaqgmdylh akniihrdmk snniflhegl
481 tvkigdfgla tvksrwsgsq qveqptgsvl wmapevirmq dnnpfsfqsd vysygivlye
541 lmtgelpysh innrdqiifm vgrgyaspdl sklykncpka mkrlvadcvk kvkeerplfp
601 qilssiellq hslpkinrsa sepslhraah tedinactlt tsprlpvf
```
(NCBI Accession NP_002871.1).

CRAF A373F, comprising an alanine-to-phenylalanine mutation as described herein which is homologous to KSR A587F can have an amino acid sequence

```
                                                       (SEQ ID NO: 6)
  1 mehiqgawkt isngfgfkda vfdgsscisp tivqqfgyqr rasddgkltd psktsntirv
 61 flpnkqrtvv nvrngmslhd clmkalkvrg lqpeccavfr llhehkgkka rldwntdaas
121 ligeelqvdf ldhvpltthn farktflkla fcdicqkfll ngfrcqtcgy kfhehcstkv
```

```
181 ptmcvdwsni rqlllfpnst igdsgvpalp sltmrrmres vsrmpvssqh rystphaftf
241 ntsspssegs lsqrqrstst pnvhmvsttl pvdsrmieda irshsesasp salsssspnnl
301 sptgwsqpkt pvpaqrerap vsgtqeknki rprgqrdssy yweieasevm lstrigsgsf
361 gtvykgkwhg dvfvkilkvv dptpeqfqaf rnevavlrkt rhvnillfmg ymtkdnlaiv
421 tqwcegssly khlhvqetkf qmfqlidiar qtaqgmdylh akniihrdmk snniflhegl
481 tvkigdfgla tvksrwsgsq qveqptgsvl wmapevirmq dnnpfsfqsd vysygivlye
541 lmtgelpysh innrdqiifm vgrgyaspdl sklykncpka mkrlvadcvk kvkeerplfp
601 qilssiellq hslpkinrsa sepslhraah tedinactlt tsprlpvf.
                                                       15
```

A nucleic acid of the present teachings can encode KSR, and have a nucleotide sequence such as

```
                                                                    (SEQ ID NO: 7)
   1 ctggacccct gccagggaag gggtcctcag acttgaggtt gccagctcag atgtggggct
  61 gctgatacta ggtgactgga ctgatgttct gttctagatg aaactccttg aggggaccat
 121 ttgaaaaggc ttgatgtgct gcccaaagcc cccttcagag ctgacttctc cacccccagc
 181 tgccgtgagc cttggctgct gacagctcat agctgagtcc ctcccgtgaa gtcaccttct
 241 gctgaagggt acatcctctc ccaaggcgaa gctggtccgt tacatttgta agcagaggca
 301 gtgcaagctg agcgtggctc ccggtgagag gaccccagag ctcaacagct accccgctt
 361 cagcgactgg ctgtacactt tcaacgtgag gccggaggtg gtgcaggaga tcccccgaga
 421 cctcacgctg gatgccctgc tggagatgaa tgaggccaag gtgaaggaga cgctgcggcg
 481 ctgtggggcc agcggggatg agtgtggccg tctgcagtat gccctcacct gcctgcggaa
 541 ggtgacaggc ctgggagggg agcacaagga ggactccagt tggagttcat ggatgcgcg
 601 gcgggaaagt ggctcagggc cttccacgga caccctctca gcagccagcc tgccctggcc
 661 cccagggagc tcccagctgg gcagagcagg caacagcgcc cagggcccac gctccatctc
 721 cgtgtcagct ctgcccgcct cagactcccc cacccccagc ttcagtgagg gcctctcaga
 781 cacctgtatt cccctgcacg ccagcggccg gctgaccccc cgtgccctgc acagcttcat
 841 caccccgccc accacacccc agctgcgacg gcacaccaag ctgaagccac cacggacgcc
 901 cccccaccc agccgcaagg tcttccagct gctgcccagc ttccccacac tcacccggag
 961 caagtcccat gagtctcagc tggggaaccg cattgatgac gtctcctcga tgaggtttga
T1021 tctctcgcat ggatccccac agatggtacg gagggatatc gggctgtcgg tgacgcacag
1081 gttctccacc aagtcctggc tgtcgcaggt ctgccacgtg tgccagaaga gcatgatatt
1141 tggagtgaag tgcaagcatt gcaggttgaa tgtcacaac aaatgtacca agaagccc
1201 tgcctgtaga atatccttcc tgccactaac tcggcttcgg aggacagaat ctgtcccctc
1261 ggacatcaac aacccggtgg acagagcagc cgaaccccat tttggaaccc tccccaaagc
1321 actgacaaag aaggagcacc ctccggccat gaatcacctg gactccagca gcaaccttc
1381 ctccaccacc tcctccacac cctcctcacc ggcgcccttc ccgacatcat ccaacccatc
1441 cagcgccacc acgccccca acccctcacc tggccagcgg gacagcaggt tcaacttccc
1501 agctgcctac ttcattcatc atagacagca gtttatctttt ccagtgccat ctgctggcca
1561 ttgctggaaa tgcctcctta ttgcagaaag tttaaaggaa aacgctttca acatttcagc
1621 ctttgcacac gcagccccgc tccctgaagc tgccgacggt acccggctcg atgaccagcc
1681 gaaagcagat gtgttggaag ctcacgaagc ggaggctgag gagccagagg ctggcaagtc
```

-continued

```
1741  agaggcagaa gacgatgagg acgaggtgga cgacttgccg agctctcgcc ggccctggcg
1801  gggccccatc tctcgcaagg ccagccagac cagcgtgtac ctgcaggagt gggacatccc
1861  cttcgagcag gtagagctgg gcgagcccat cgggcagggc cgctgggccc gggtgcaccg
1921  cggccgctgg catggcgagg tggccattcg cctgctggag atggacggcc acaaccagga
1981  ccacctgaag ctcttcaaga aagaggtgat gaactaccgg cagacgcggc atgagaacgt
2041  ggtgctcttc atgggggcct gcatgaaccc gccccacctg ccattatca ccagcttctg
2101  caagggggcgg acgttgcact cgtttgtgag ggaccccaag acgtctctgg acatcaacaa
2161  gacgaggcaa atcgctcagg agatcatcaa gggcatggga tatcttcatg ccaagggcat
2221  cgtacacaaa gatctcaaat ctaagaacgt cttctatgac aacggcaagg tggtcatcac
2281  agacttcggg ctgtttggga tctcaggcgt ggtccgagag ggacggcgtg agaaccagct
2341  aaagctgtcc cacgactggc tgtgctatct ggcccctgag attgtacgcg agatgacccc
2401  cgggaaggac gaggatcagc tgccattctc caaagctgct gatgtctatg catttgggac
2461  tgtttggtat gagctgcaag caagagactg gcccttgaag aaccaggctg cagaggcatc
2521  catctggcag attggaagcg gggaaggaat gaagcgtgtc ctgacttctg tcagcttggg
2581  gaaggaagtc agtgagatcc tgtcggcctg ctgggctttc gacctgcagg agagacccag
2641  cttcagcctg ctgatggaca tgctggagaa acttcccaag ctgaaccggc ggctctccca
2701  ccctggacac ttctggaagt cagctgagtt gtaggcctgg ctgccttgca tgcaccaggg
2761  gctttcttcc tcctaatcaa caactcagca ccgtgacttc tgctaaaatg caaaatgaga
2821  tgcgggcact aacccagggg atgccacctc tgctgctcca gtcgtctctc tcgaggctac
2881  ttcttttgct ttgttttaaa aactggcccct ctgccctctc cacgtggcct gcatatgccc
2941  aagtaactgc tctcagagga tcccactaac tgagctccct ccaaggcagt ctgggcagct
3001  tctaactacc ttcctggaca tgactgattg ctcccgtgtt cttctgaggg ctggtcttgt
3061  ttttgtttgg gtggctctgt ctcactgcta acaccttagt gagatgcctt ccaccctcct
3121  gagcacacca gcctcccact gggtgtgtgc ctagtgcggg gcgggcggag gttgggaggg
3181  tgttggcttg gcttttaacc tgtggggatt ttgtccaaca aggagtggaa tgatttcaga
3241  gctgccctga ggctggcacc ctggtcacag gaaccctctg cgctggctcc tgtctcagtc
3301  ccctctgtag agttagatca gaagacacag aaagttctgt ggccatgaaa gataccagct
3361  tggaagggtt gtgtcttcag tggcaccctc agaaaaattg tcttaaagca aagaggtacc
3421  tggctccaga caattttttct gatgaaaaca aagtctctgc cccgtcccca ccctgccacc
3481  ctggcaaagt tacttccttt acagctgccc agtgtaccat agaccagacc ccaggtcagc
3541  atttgtcaag agcatggctg ctgagtcccc tgtggcagtc aatgcactgt ttaccaaatg
3601  caggtttctg ttctccctcc ccagcaagac ctgctgaacc cagatctctg gaatggggcc
3661  ctaggaattt gcatttcaac ctgcttccca ggtggccctg atgcaccccca gtattagagt
3721  ttattgctaa aaggaacatg ccctgtcact cctggtatcc tgggagtcat gtttctcttc
3781  tctctcagtt ctacttggag caagagcttt cctgggctgc aaatgagaaa acaattccta
3841  ggaacccaca gcagtactga gcatgctggg agcttgggac ttggagatga atgagccacc
3901  gttgctgctc caagtaggac tacttggagt gtagctgagg ccttggacgc agtatgacca
3961  ggggcagctc tgccagggct gttggccaat cagtcatttt catttcttgt tggaggccag
4021  gtcctctgct gaactcattt cctagctagt gttaccctaa ttctgatgaa gatcaatggg
4081  gctataattc ttgttttttgt tcctctttgc agcattaaca gcagcaaagt tgtaccccgg
```

```
-continued
4141 tttgaaaggt ttggcttggg cgtcctggag tccagtaatc caaagatgta gccagccata 4201 tggtttttcg ctgctgatct cttcttttt aaaatgtgtt tctgaaacat cccaacaacc 4261 accacgacaa aaaaacactg cctgcccagc gctgcaaacc aggagcacac gtcctagatt 4321 cagactgttg gccataaacc ccactcggga gatggagctg cacctgctat ttcttaaaat 4381 gacaccacca acaaccaaac ctgtcatgac agacagcaaa tgtttacacg tatatttctc 4441 ctgagtgaac ctgatgtttt acaataggta ataataaaaa cagtctgtgc aaaaaaaaaa 4501 aaaaaaaaaa aaaaaaaaaa aaaaaaaaaa aaaaaaaaaa aaaaaaaaaa aa
```

(NCBI Accession NM_014238).

The present teachings include a nucleic acid sequence encoding KSR comprising an A587F mutation. The present teachings also include a nucleic acid sequence encoding KSR comprising an L591F mutation. Such mutations can be introduced into a nucleic acid encoding KSR using routine methods well known to skilled artisans, such as, for example, introduction of mutant sequences using polymerase chain reactions.

The present teachings also include nucleic acids encoding kinases or pseudokinases, wherein the encoded polypeptide comprises a mutation homologous to A587F of KSR. Such nucleic acids can comprise a DNA or an RNA.

In various configurations, a nucleic acid of the present teachings can be an oligonucleotide which comprises at least 10 nucleotides, at least 15 nucleotides, or at least 20 nucleotides, up to 50 nucleotides, about 50 nucleotides, up to 60 nucleotides, about 60 nucleotides, up to 70 nucleotides, or about 70 nucleotides, and can comprise a sequence encoding an amino acid sequence comprising A587F of KSR, or a homologous alanine-to-phenylalanine mutation of another kinase or pseudokinase. In some configurations, an oligonucleotide can be complementary to a sequence encoding an A587F of KSR, or a homologous alanine-to-phenylalanine mutation of another kinase or pseudokinase.

In some embodiments, the present teachings include a mutated form of KSR comprising a leucine 591 to phenylalanine mutation (L591F, with amino acid numbering in reference to the sequence of Mus musculus KSR). In various configurations, the ability of this KSR mutant to act as a scaffold can be impaired. In various configurations, this mutant of KSR can have constitutively active kinase activity which is independent of BRAF and CRAF. In some configurations, this mutated form does not dimerize with CRAF. Without being limited by theory, the failure of this mutant to dimerize with CRAF suggested to the present inventors that the scaffolding function of KSR with CRAF might not be sufficient for KSR's function. The present inventors further disclose that while wild type KSR exhibits no kinase activity when expressed alone, homodimerization of KSR can result in KSR kinase activity, such as phosphorylation of a substrate, for example a downstream target such as MEK or a oligopeptide substrate containing a target sequence, such as an oligopeptide consisting of a target sequence of MEK that includes an amino acid that is subject to phosphorylation by KSR. The inventors further determined that KSR can be a bona fide kinase whose activity can be required for activation of MEK.

Human KSR L591F of the present teachings can have amino acid sequence (SEQ ID NO. 8)
```
  1 mneakvketl rrcgasgdec grlqyaltcl rkvtglggeh kedsswssld arresgsgps 61 tdtlsaaslp wppgssqlgr agnsaqgprs isvsalpasd sptpsfsegl sdtciplhas 121 grltpralhs fitppttpql rrhtklkppr tppppsrkvf qllpsfptlt rskshesqlg 181 nriddvssmr fdlshgspqm vrrdiglsvt hrfstkswls qvchvcqksm ifgvkckhcr 241 lkchnkctke apacrisflp ltrlrrtesv psdinnpvdr aaephfgtlp kaltkkehpp 301 amnhldsssn pssttsstps spapfptssn pssattppnp spgqrdsrfn fpaayfihhr 361 qqfifpvpsa ghcwkcllia eslkenafni safahaaplp eaadgtrldd qpkadvleah 421 eaeaeepeag kseaeddede vddlpssrrp wrgpisrkas qtsvylqewd ipfeqvelge 481 pigqgnvgrv hrgrwhgeva irl_f_emdghn qdhlklfkke vmnyrqtrhe nvvlfmgacm 541 npphlaiits fckgrtlhsf vrdpktsldi nktrqiaqei ikgmgylhak givhkdlksk 601 nvfydngkvv itdfglfgis gvvregrren qlklshdwlc ylapeivrem tpgkdedqlp 661 fskaadvyaf gtvwyelqar dwplknqaae asiwqigsge gmkrvltsvs lgkevseils 721 acwafdlqer psfsllmdml eklpklnrrl shpghfwksa el.
```

In some embodiments, the present teachings include assays for detecting dimerization of kinases as well as methods of screening compounds as activators or inhibitors of kinase activation. In some configurations, an inhibitor of kinase dimerization can be effective as an anti-cancer therapeutic.

In various configurations, a dimerization assay of these embodiments can comprise expressing in a cell a first fusion polypeptide comprising a sequence of a kinase such as KSR or a dimerization domain thereof, and an amino terminal portion of an enzyme, as well as a expressing in the cell a second fusion polypeptide comprising a sequence of a binding partner of the kinase, and a carboxy terminal portion of the enzyme. The binding partner can be the same kinase, another kinase, or a dimerization domain thereof. Upon expression of both fusion constructs and in the absence of an inhibitor, the amino terminal and carboxy terminal portions of the enzymes interact to provide a functioning enzyme which can have enzyme activity which can be detected by methods well known to skilled artisans. In various configurations, the enzyme can be, without limitation a luciferase or a beta-galactosidase. In various configurations the luciferase can be a Ranilla luciferase. In various embodiments, a screen for an inhibitor of dimerization can comprise contacting a cell expressing both fusion polypeptides with a candidate inhibitor, and performing an assay for the enzyme. A reduction in enzyme activity compared to a control can indicate that the candidate inhibitor can inhibit dimerization of the kinase of the first fusion polypeptide with its binding partner comprised by the second fusion polypeptide. For example and without limitation, a kinase and binding partner of fusion polypeptides can be, respectively KSR/KSR, KSR/BRAF, KSR/CRAF, BRAF/BRAF, BRAF/CRAF, or CRAF/CRAF, or mutants thereof.

In some embodiments, the present teachings includes nucleic acids that encode the first fusion polypeptide operably linked to a promoter, and nucleic acids that encode the second fusion polypeptide operably linked to a promoter. In each case, the nucleic acid can be comprised by a vector such as a plasmid or virus.

In some embodiments, the present teachings include cells and cell lines comprising the nucleic acids. In various configurations, these cell cells lines can be stable transformations or transient transformations. A cell of these embodiments can be any suitable host, such as, without limitation, HeLa, A375, HEK293, mouse embryonic fibroblast, or CHO.

In some embodiments, the present teachings include cell lines that are resistant to BRAF inhibition but dependent on KSR. In some embodiments, these cells can be stably transfected cells expressing BRAF V600E and NRASV12 or KRASV12. In some embodiments, these cells can be stably transfected cells expressing BRAF V600E and TPL2/COT. In various configurations, the cells can be, without limitation, HeLa transformed with BRAF V600E as well as NRASV12, KRASV12 or TPL2/COT, or a tumor-derived cell line comprising a BRAF V600E mutation and transformed with NRASV12, KRASV12 or TPL2/COT. In various configurations, a tumor-derived cell line comprising a BRAF V600E mutation can be a melanoma cell line such as, without limitation, A375, MALME-3M, Colo829, Colo38, SK-MEL28, SK-MEL5, HT144, LOX, A2058, or a breast cancer cell line such as, without limitation, MDA-MB-435.

The present teachings include the following aspects.
1. A mutant kinase or pseudokinase, comprising an alanine-to-phenylalanine mutation of KSR A587F, or a homologous alanine-to-phenylalanine mutation in a homologue thereof.
2. A mutant kinase or pseudokinase in accordance with aspect 1, comprising an alanine-to-phenylalanine mutation A587F of KSR.
3. A mutant kinase or pseudokinase in accordance with aspect 1, comprising an alanine-to-phenylalanine mutation of a Raf kinase at an alanine at a sequence homologous to KSR A487.
4. A mutant kinase or pseudokinase in accordance with aspect 3, comprising an alanine-to-phenylalanine mutation of a Raf kinase, selected from the group consisting of BRAF A481 F and CRAF A373F.
5. A mutant kinase or pseudokinase in accordance with aspect 1, comprising an alanine-to-phenylalanine mutation of a mammalian kinase or pseudokinase, wherein the alanine is homologous to KSR A487.
6. A mutant kinase or pseudokinase in accordance with aspect 1, comprising an alanine-to-phenylalanine mutation of a human kinase or pseudokinase, wherein the alanine is homologous to KSR A487.
7. A mutant kinase or pseudokinase in accordance with aspect 1, comprising an alanine-to-phenylalanine mutation A70F of Protein Kinase A.
8. A mutant kinase or pseudokinase in accordance with aspect 1, comprising an alanine-to-phenylalanine mutation in a kinase at a sequence homologous to A70F of Protein Kinase A.
9. A nucleic acid encoding a mutant kinase or pseudokinase of any one of aspects 1-8.
10. A cell comprising a mutant kinase or pseudokinase of any one of aspects 1-8.
11. A cell in accordance with aspect 10, further comprising a dimerization partner of the mutant kinase or pseudokinase.
12. A cell comprising a nucleic acid encoding a mutant kinase or pseudokinase of any one of aspects 1-8.
13. A cell in accordance with aspect 12, further comprising a nucleic acid encoding a dimerization partner of the mutant kinase or pseudokinase.
14. A method of screening a compound for activity as a kinase inhibitor or agonist, comprising:
providing a mutant kinase or pseudokinase of any one of aspects 1-8;
forming a mixture comprising the kinase or pseudokinase and a candidate inhibitor or agonist; and
measuring kinase activity in the mixture.
15. A method of screening a compound for activity as an inhibitor of kinase dimerization, comprising:
providing a cell of any one of aspects 10-13;
contacting the cell with a candidate inhibitor of kinase dimerization; and
measuring dimer formation or stability in the cell.
16. A method of screening a compound for activity as an inhibitor of kinase dimerization, comprising:
providing a mutant kinase or pseudokinase of any one of aspects 1-8:
forming a mixture comprising the kinase or pseudokinase, a dimerization partner of the kinase or pseudokinase, and a candidate inhibitor of kinase dimerization; and
measuring dimer formation or stability in the mixture.
17. A method of screening a compound for activity as an inhibitor of kinase dimerization in accordance with aspect 16, wherein the measuring dimer formation comprises using a complementation assay.
18. A method of screening a compound for activity as an inhibitor of kinase dimerization in accordance with aspect 16, wherein the measuring dimer formation comprises using a luciferase complementation assay.

19. A method of screening a compound for activity as an inhibitor of kinase dimerization in accordance with aspect 16, wherein the measuring dimer formation comprises using a fluorescent protein complementation assay.

20. A method for selecting a candidate drug which interferes with an activity of a kinase or pseudokinase, the method comprising: (a) providing a three-dimensional structure of the kinase or pseudokinase mutant of any one of aspects 1-8 in complex with an dimerization partner: and (b) designing a compound predicted to bind the complex.

21. A method for designing a compound which interferes with an activity of a kinase or pseudokinase, the method comprising: (a) providing on a digital computer a three-dimensional structure of a complex comprising a kinase or pseudokinase mutant of any one of aspects 1-8 and a dimerization partner; and (b) using software comprised by the digital computer to design a compound which is predicted to bind to the complex.

22. A method according to aspect 21, further comprising: (c) synthesizing the compound; and (d) evaluating the compound for an ability to interfere with dimerization of the kinase or pseudokinase mutant.

23. A crystal comprising a kinase or pseudokinase mutant of any one of aspects 1-8 and a dimerization partner.

24. A computer image of a comples comprising a mutant kinase or pseudokinase of any one of aspects 1-8 and a dimerization partner thereof.

25. A mutant kinase or pseudokinase, comprising a leucine-to-phenylalanine mutation of KSR L591F, or a homologous leucine-to-phenylalanine mutation in a homologue thereof.

26. A mutant kinase or pseudokinase in accordance with aspect 25, comprising a leucine-to-phenylalanine mutation L591F of KSR.

27. A mutant kinase or pseudokinase in accordance with aspect 25, comprising a leucine-to-phenylalanine mutation of a Raf kinase at a leucine at a sequence homologous to KSR L591.

28. A mutant kinase or pseudokinase in accordance with aspect 25, comprising a leucine-to-phenylalanine mutation of a mammalian kinase or pseudokinase, wherein the leucine is homologous to KSR L591.

30. A mutant kinase or pseudokinase in accordance with aspect 25, comprising a leucine-to-phenylalanine mutation of a human kinase or pseudokinase, wherein the leucine is homologous to KSR L591.

31. A nucleic acid encoding a mutant kinase or pseudokinase of any one of aspects 25-30.

32. A cell comprising a mutant kinase or pseudokinase of any one of aspects 25-30.

33. A cell in accordance with aspect 32, further comprising a dimerization partner of the mutant kinase or pseudokinase encoded by a nucleic acid heterologous to the cell.

34. A cell comprising a nucleic acid encoding a mutant kinase or pseudokinase of any one of aspects 25-30.

35. A cell in accordance with aspect 9, further comprising a nucleic acid heterologous to the cell, said nucleic acid encoding a dimerization partner of the mutant kinase or pseudokinase encoded by a nucleic acid heterologous to the cell.

36. A method of screening a compound for activity as a kinase inhibitor or agonist, comprising:
providing a mutant kinase or pseudokinase of any one of aspects 25-30:
forming a mixture comprising the kinase or pseudokinase and a candidate inhibitor or agonist; and
measuring kinase activity in the mixture.

37. A method of screening a compound for activity as an inhibitor of kinase dimerization, comprising:
providing a cell of any one of aspects 32-35;
contacting the cell with a candidate inhibitor of kinase dimerization; and
measuring dimer formation or stability in the cell.

38. A method of screening a compound for activity as an inhibitor of kinase dimerization, comprising:
providing a mutant kinase or pseudokinase of any one of aspects 32-35;
forming a mixture comprising the kinase or pseudokinase, a dimerization partner of the kinase or pseudokinase, and a candidate inhibitor of kinase dimerization; and
measuring dimer formation or stability in the mixture.

39. A method of screening a compound for activity as an inhibitor of kinase dimerization in accordance with aspect 38, wherein the measuring dimer formation comprises a complementation assay.

40. A method of screening a compound for activity as an inhibitor of kinase dimerization in accordance with aspect 38, wherein the measuring dimer formation comprises a luciferase complementation assay.

41. A method of screening a compound for activity as an inhibitor of kinase dimerization in accordance with aspect 38, wherein the measuring dimer formation comprises using a fluorescent protein complementation assay.

42. A method for selecting a candidate drug which interferes with an activity of a kinase or pseudokinase, the method comprising: (a) providing a three-dimensional structure of the kinase or pseudokinase mutant of any one of aspects 25-30 in complex with a dimerization partner; and (b) designing a compound predicted to bind the complex.

43. A method for designing a compound which interferes with an activity of a kinase or pseudokinase, the method comprising: (a) providing on a digital computer a three-dimensional structure of a complex comprising a kinase or pseudokinase mutant of any one of aspects 25-30 and a dimerization partner; and (b) using software comprised by the digital computer to design a compound which is predicted to bind to the complex.

44. A method according to aspect 43, further comprising: (c) synthesizing the compound: and (d) evaluating the compound for an ability to interfere with dimerization of the kinase or pseudokinase mutant.

45. A crystal comprising a kinase or pseudokinase mutant of any one of aspects 25-30 and a dimerization partner.

46. A computer image of a comples comprising a mutant kinase or pseudokinase of any one of aspects 25-30 and a dimerization partner thereof.

47. A fusion polypeptide comprising:
A first inactive portion of an enzyme; and
a KSR dimerization sequence, wherein the portion can be activated by complementation.

48. A fusion polypeptide in accordance with aspect 47, wherein the first inactive portion of the enzyme is selected from the group consisting of an amino terminal portion of the enzyme and a carboxy terminal portion of the enzyme.

49. A polypeptide in accordance with aspect 47, wherein the KSR dimerization domain comprises an A587F mutation.

50. A polypeptide in accordance with aspect 47, wherein the enzyme is a luciferase.

51. A polypeptide in accordance with aspect 47, wherein the enzyme is a Ranilla luciferase.

52. A polypeptide in accordance with aspect 47, wherein the KSR dimerization sequence is comprised by a sequence of a full length KSR.

53. A fusion polypeptide comprising:
   a second inactive enzyme portion complementary to the first inactive portion of an enzyme of aspect 47; and
   a polypeptide sequence of a KSR kinase binding partner or a KSR-binding domain thereof.
54. A fusion polypeptide in accordance with aspect 53, wherein the polypeptide sequence of a KSR kinase binding partner or a KSR-binding domain thereof is a polypeptide sequence selected from the group consisting of the polypeptide sequence of KSR, the polypeptide sequence of BRAF, the polypeptide sequence of CRAF, the polypeptide sequence of a KSR dimerization domain, the polypeptide sequence of a BRAF dimerization domain and the polypeptide sequence of a CRAF dimerization domain.
55. A cell in vitro comprising:
   the polypeptide of any one of aspects 47-52; and
   the polypeptide of any one of aspects 53-54,
whereby in the absence of an inhibitor, the first polypeptide and the second polypeptide form a complex, thereby activating activity of the enzyme.
56. A cell in accordance with aspect 55, wherein the polypeptide of any one of aspects 47-52 comprises the amino terminal portion of the enzyme and a KSR dimerization sequence, and the polypeptide of any one of aspects 53-54 comprises the carboxy terminal portion of the enzyme and a dimerization domain of a KSR dimerization partner.
57. A cell in accordance with aspect 55, wherein the polypeptide of any one of aspects 47-52 comprises the carboxy terminal portion of the enzyme and a KSR dimerization sequence, and the polypeptide of any one of aspects 53-54 comprises the amino terminal portion of the enzyme and a dimerization domain of a KSR dimerization partner.
58. A cell in accordance with any one of aspects 55-57, wherein the enzyme is a luciferase.
59. A cell in accordance with any one of aspects 55-58, wherein the enzyme is a Ranilla luciferase.
60. A cell in accordance with any one of aspects 55-59, wherein the cell is a eukaryotic cell.
61. A cell in accordance with aspect 60, wherein the eukaryotic cell is a mammalian cell.
62. A cell in accordance with aspect 61, wherein the mammalian cell is selected from the group consisting of a human cell, a murine cell, and rat cell.
63. A method of screening for an inhibitor of KSR dimerization, comprising:
   providing a culture comprising a cell in accordance with any one of aspects 55-59;
   contacting the culture with a candidate inhibitor of KSR dimerization; and
   detecting the presence, absence, or quantity of activity of the enzyme, whereby a decrease in activity compared to a control indicates that the candidate inhibitor has activity as a KSR dimerization inhibitor.

BRIEF DESCRIPTION OF THE DRAWINGS

FIG. 1A illustrates that GDC0879 but not PLX4720 induces dimers between BRAF and CRAF. Cells overexpressing myc-CRAF and BRAF were treated with drug for 1 hour and CRAF immunoprecipitates were immunoblotted for BRAF and CRAF (myc). FIG. 1B illustrates that GDC0879 but not PLX4720 can induce dimer formation between FLAG-KSR and BRAF. KSR immunoprecipitates were prepared from cells overexpressing FLAG-KSR and BRAF after treatment with the indicated drug for 1 hour and immunoblotted using antibodies to BRAF. FIG. 1C illustrates that both GDC0879 and PLX4720 induce dimer formation between KSR and CRAF. FLAG-KSR immunoprecipitates were prepared from cells overexpressing FLAG-KSR and myc-CRAF after treatment with the indicated drug for 1 hour and immunoblotted for CRAF using myc antibodies. FIG. 1D illustrates lysates, obtained from wild-type and KSR-deficient fibroblasts transfected with RasV12 and treated with GDC-0879 for 1 hour, that were immunoblotted for phospho-ERK1 and 2, ERK2 and RasV12. FIG. 1E illustrates lysates, obtained from wild-type and KSR-deficient fibroblasts transfected with RasV12 and treated with PLX4720 for 1 hour, that were immunoblotted for phospho-ERK1 and 2, ERK2 and RasV12. FIG. 1F illustrates the function of the CRAF/KSR dimer by co-expressing both proteins and using PLX4720 to induce dimer formation between the two proteins and that KSR and CRAF cooperate to activate MEK. FIG. 1G illustrates that treatment of cells with PLX4720 induced kinase activity towards MEK in the KSR immunoprecipitates and only occurred when KSR and CRAF were co-expressed together.

FIG. 2A illustrates mutagenesis performed to substitute phenylalanine or valine for A587 of mouse 6× His-KSR1. Each mutant was expressed in cells, purified using. Ni2+-agarose and tested for ATP binding using a biotinylated-ATP analog after UV cross-linking and immunoblotting for the presence of biotin. FIG. 2B illustrates KSR deficient fibroblasts reconstituted with YFP-fused to wild-type or mutated KSR and sorted to generate cell lines with similar expression levels. Cells were stimulated with EGF for the indicated times and cell lysates were immunoblotted with an antibody to phosphorylated ERK (pERK). FIG. 2C illustrates that cell transformation by RasV12 is dependent on KSR16 using transduced cell lines generated with RasV12 (FIG. 2B) and assessing cell transformation by focus-formation. FIG. 2D illustrates analogous mutations in dKSR (A703V and A703F) expressed them in *Drosophila* S2 cells with dRAF; the A703V mutant was still able to activate MEK while the A703F mutant had no effect. FIG. 2E illustrates dBRAF immunoprecipitates prepared from S2 cells that coexpressed dBRAF with either wild-type or mutated dKSR and immunoblotted for dKSR(V5) and dBRAF(pyo). FIG. 2F illustrates constitutive dimer formation between A587F KSR and CRAF. FLAG-KSR immunoprecipitates were prepared from lysates from cells expressing A587F FLAG-KSR with myc-CRAF and immunoblotted for CRAF (myc). FIG. 2G illustrates that there was no effect of A587F KSR mutation on binding to BRAF. FIG. 2H illustrates that an A587F KSR mutation does not effect MEK binding. KSR immunoprecipitates from cell co-expressing GFP-MEK1 and WT or KSR mutants were immunoblotted for GFP-MEK and KSR (FLAG).

FIGS. 3A-C illustrate modeling the structural effects of the alanine-to-phenylalanine change in CRAF and BRAF. FIG. 3A illustrates the position of residues constituting the hydrophobic spines of CRAF crystallized with a Type I inhibitor (stabilizes the closed and ATP bound form of the kinase). FIG. 3B illustrates hydrophobic spine residues in BRAF bound to a Type II inhibitor (binds to the open conformation preventing closing of the cleft). FIG. 3C illustrates a simulated structure of CRAF where A373 is replaced with Phe.

FIGS. 4A-E illustrate that an A-to-F mutation in RAF can induce dimer formation and can activate ERK signaling. FIG. 4A illustrates co-immunoprecipitation assays that show that BRAF A481 F form constitutive dimers with CRAF and that CRAF A373F form constitutive dimers with BRAF. FIG. 4B illustrates that the CRAF A373F mutant also forms constitutive dimers with KSR but the BRAF A481 F did not enhance basal dimer formation with KSR. FIG. 4C illustrates that three AF mutants (BRAF, CRAF and KSR) were over-expressed in cells and were tested for their effects on endogenous ERK activation. FIG. 4I) illustrates WI and ksr−/− MEFs transfected with BRAF(A481 F). 24 hours later, cells were treated with or without 20 µM GDC0879 for 60 min, before lysis. ERK phosphorylation was assessed by immunoblotting. Immunoblotting for total ERK2 was used as a loading control. FIG. 4E illustrates WT and ksr−/− MEFs transfected with BRAF(V600E) 24 hours later, cells were treated with or without 20 µM GDC0879 for 60 min, before lysis. ERK phosphorylation was assessed by immunoblotting. Immunoblotting for total ERK2 was used as a loading control.

DETAILED DESCRIPTION

Figure 1:
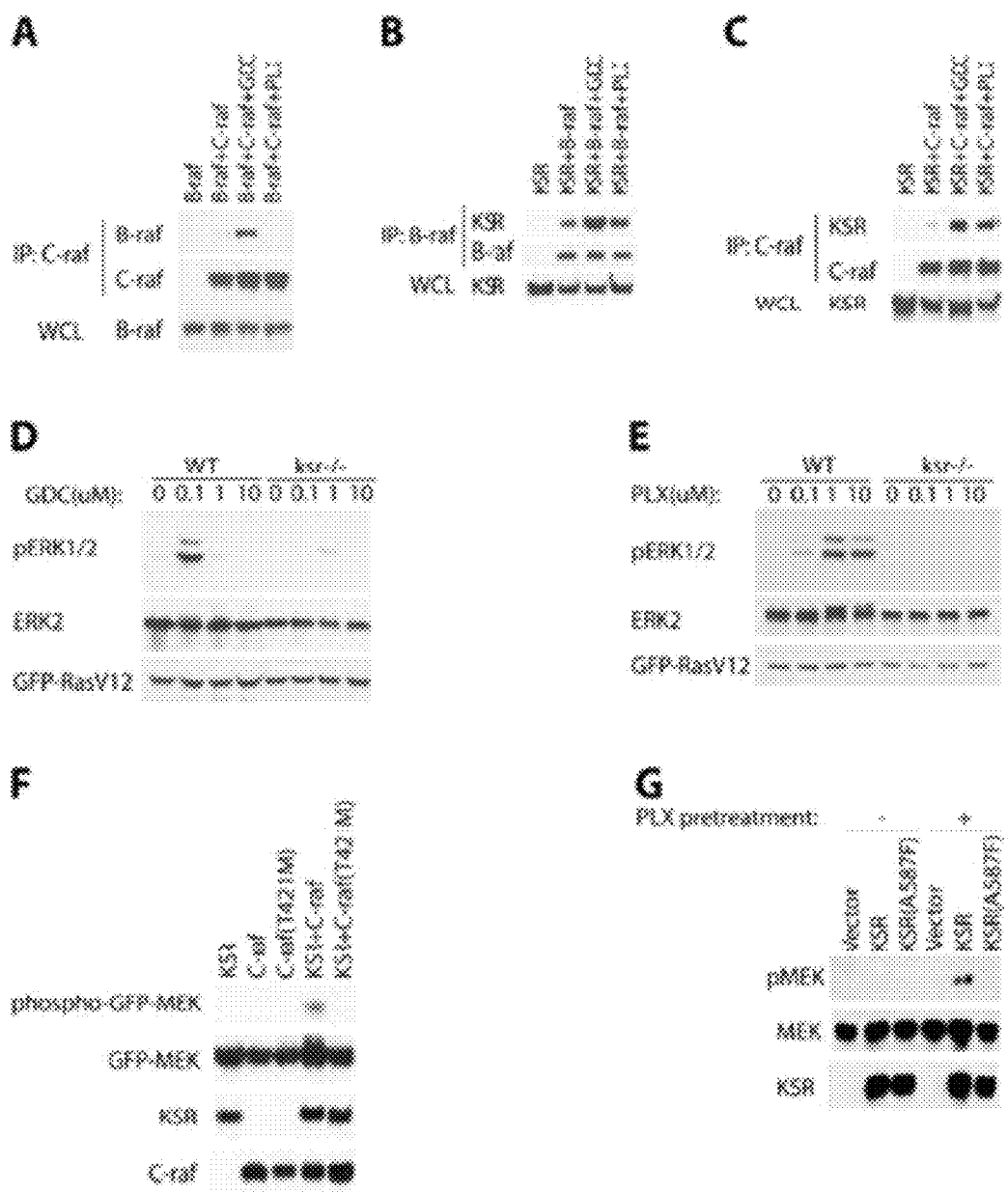
FIGS. 1A-G illustrate that RAF inhibitors can induce dimer formation between KSR and RAF, and activate KSR by CRAF.

The present inventors demonstrate that the activity of both kinase-active and -inactive BRAF mutants require KSR for their function. In various configurations, KSR is required when BRAF is directly phosphorylating MEK (V600E) or when BRAF is activating MEK through activation of CRAF (kinase-dead BRAF). KSR can function to bring both MEK and BRAF to CRAF. Since MEK and BRAF binding to KSR are constitutive (McKay, M. M., Proc. Nat'l. Acad. Sci. USA 106, 11022-11027, 2009), activation of the pathway can involve the induced recruitment of CRAF.

The present inventors demonstrate that MEK phosphorylation can be mediated by KSR catalytic activity.

By mutating the conserved Ala in the catalytic spine to Phe of KSR, CRAF and BRAF, the present inventors created an adenine mimetic that can stabilize the closed conformation of the kinase core that includes the dimer interface but renders the kinase inactive. These pseudokinases that were generated assume a conformation that resembles the active kinase but because they can't bind ATP, they are unambiguously catalytically dead. All previous known strategies to inactivate kinase activity results in a dynamic kinase with impaired scaffolding function.

Because some of the scaffolding functions of kinases require the active conformation, the present inventors demonstrate that the alanine to phenylalanine mutant is unique because it can stabilize the scaffolding function. The mutants can be used to separate the scaffolding properties of BRAF, CRAF and KSR from their catalytic activity. In the case of BRAF, the A481 F mutant, can constitutively activate MEK and ERK in a manner that is kinase independent, RAS independent but KSR dependent. The RAS independence is similar to the V600E mutant and both the V600E and A481 F mutations can uncouple the inhibitory amino-terminal domain from the kinase domain. Since the AF mutant lacks catalytic activity, the scaffolding and not the kinase function of the BRAF V600E mutant can be sufficient to account for its transformation activity.

The A587F mutant of KSR can still retain scaffolding function as it can dimerize with BRAF and CRAF and still bind to MEK. The inventors' findings establish at least two functions of KSR: it not only has the scaffolding function; ATP binding and kinase activity are also functional properties of KSR.

A mutant of the present teachings that induces the closed, active conformation but is catalytically active can be used to separate the two different functions of kinases. While BRAF could function as a scaffold alone, the requirement for both CRAF and KSR to bind to ATP for downstream activation of MEK and ERK demonstrate that both can function as kinases and can have distinct functions from BRAF.

By mutating the Leu to the catalytic spine Phe of KSR, the present inventors created a mimetic that can stabilize the closed conformation of the kinase core that excludes the dimer interface and therefore cannot bind to CRAF or BRAF. This leucine-to-phenylalanine mutant maintains a constitutively active kinase conformation but is independent of BRAF and CRAF. Furthermore, KSR L591F can bind ATP.

Methods

The methods and compositions described herein utilize laboratory techniques well known to skilled artisans, and can be found in laboratory manuals such as Sambrook, J., et al., Molecular Cloning: A Laboratory Manual, 3rd ed. Cold Spring Harbor Laboratory Press, Cold Spring Harbor, N.Y., 2001; Spector, D. L. et al., Cells: A Laboratory Manual, Cold Spring Harbor Laboratory Press, Cold Spring Harbor, N.Y., 1998; Ausubel, F. M., et al., ed., Current Protocols in Molecular Biology, Wiley Interscience, 2003. These and all other publications cited in this disclosure are incorporated herein by reference, each in its entirety. As used in the description and any appended claims, the singular forms "a". "an" and "the" are intended to include the plural forms as well, unless the context indicates otherwise.

Some Examples set forth infra may include the following materials and methods.

Chemicals: PLX4720 and GDC0879 were purchased from Selleck Chemicals.

Antibodies: Phospho-ERK (T202-Y204) and phospho-MEK (S217/S221) antibodies were purchased from Cell Signaling.

Dimerization experiments: For most experiments, constructs for wild-type and mutated BRAF, CRAF and KSR1 were appended with epitope tags (FLAG, 6× His, Myc, GFP) and were expressed by transient transfection into 293T cells. Cells were lysed in a buffer containing 1% NP40 and 0.1% deoxycholate. Cells were pretreated with drugs for 1 hour prior to lysis. Immunoprecipitates were analyzed by gel electrophoresis and immunoblotted after transfer to nitrocellulose membranes using standard methods.

ATP binding assay: WT and mutated KSR1 constructs epitope tagged with 6× His were expressed in 293T cells and purified using Ni-NTA agarose. ATP binding was assessed by incubating the samples with 100 uM biotin-azido-ATP (2-azidoadeosine, 5' triphosphate [γ]---5-biotinpentylamine, Affinity Probes) in a buffer containing 20 mM $Na_2HPO_4$/$NaH_2PO_4$ (pH 7.2) and 10 mM $MgCl_2$. After incubation on ice for 5 min, samples were irradiated by UV for 2 min. The ATP-crosslinked KSR or mutants in samples were examined by SDS-PAGE and Western blotting with strepavidin-HRP.

Kinase reactions: Cells transfected with various constructs were treated or not with PLX4720 for 1-2 hours. Cells were lysed with 1% NP40 and immunoprecipitates prepared. In vitro kinase reactions were performed in a standard buffer with 10 mM $MgCl_2$, with 1 ug of kinase dead MEK, and 100 uM cold ATP. In some experiments, to inhibit contaminating Raf activity, 50 uM PLX4720 was preincubated with the reactions.

EXAMPLES

The present teachings including descriptions provided in the Examples that are not intended to limit the scope of any claim or aspect. Unless specifically presented in the past tense, an example can be a prophetic or an actual example. The following non-limiting examples are provided to further illustrate the present teachings. Those of skill in the art should, in light of the present disclosure, appreciate that many changes can be made in the specific embodiments that are disclosed and still obtain a like or similar result without departing from the spirit and scope of the present teachings.

Example 1

This example demonstrates that BRAF inhibitors can induce KSR/RAF dimers.

In these experiments, two different RAF inhibitors, GDC0879 and PLX4720 were used. While the drugs are structurally unrelated, both drugs were selected for their ability to inhibit a constitutively active form of BRAF (V600E) but also bind with lower affinities to all of the wild-type RAF isoforms (Hatzivassiliou, G., et al., Nature 464, 431-435, 2010; Therrien, M., et al., Cell 83, 879-888, 1995). Crystallography studies show that both drugs are Type I inhibitors that induce formation of the closed conformation of the kinase (Hatzivassiliou, G., et al., Nature 464, 431-435, 201; Therrien, M., et al., Cell 83, 879-888, 1995). While previous reports showed that most RAF inhibitors induce the formation of BRAF/CRAF dimers supporting this as a potential mechanism for RAF activation (Hatzivassiliou, G., et al., Nature 464, 431-435, 2010; Heidorn, S. J., et al., Cell 140, 209-221, 2010; Poulikakos, P. I., et al., Nature 464, 427-430, 2010), this mechanism is not supported by the fact that PLX4720 cannot induce dimers between BRAF and CRAF and by the fact that drug induced ERK stimulation does not require BRAF (Hatzivassiliou, G., et al., Nature 464, 431-435, 2010; Heidorn, S. J., et al., Cell 140, 209-221, 2010; Poulikakos, P. I., et al., Nature 464, 427-430, 2010).

Since KSR can also form complexes with BRAF and with CRAF (McKay. M. M., et al., Proc. Nat'l. Acad. Sci. USA 106, 11022-11027, 2009; Rajakulendran, T., et al., Nature 461, 542-545, 2009), we tested whether RAF inhibitors could enhance dimer formation between RAF and KSR. Cells grown in serum, expressing combinations of KSR, BRAF and CRAF, were treated with both drugs. Co-immunoprecipitations were then performed to examine dimer formation.

FIG. 1: RAF inhibitors induce dimer formation between KSR and RAF, and activate KSR by CRAF. FIG. 1A. GDC0879 but not PLX4720 induces dimers between BRAF and CRAF. Cells overexpressing myc-CRAF and BRAF were treated with drug for 1 hour and CRAF immunoprecipitates were immunoblotted for BRAF and CRAF (myc). FIG. 1B. GDC0879 but not PLX4720 can induce dimer formation between FLAG-KSR and BRAF. KSR immunoprecipitates were prepared from cells overexpressing FLAG-KSR and BRAF after treatment with the indicated drug for 1 hour and immunoblotted using antibodies to BRAF. FIG. 1C. Both GDC0879 and PLX4720 induce dimer formation between KSR and CRAF. FLAG-KSR immunoprecipitates were prepared from cells overexpressing FLAG-KSR and myc-CRAF after treatment with the indicated drug for 1 hour and immunoblotted for CRAF using myc antibodies.

As reported previously (Hatzivassiliou, G., et al., Nature 464, 431-435, 2010; Heidorn, S. J., et al., Cell 140, 209-221, 2010; Poulikakos, P. I., et al., Nature 464, 427-430, 2010), GDC0879 but not PLX4720 induced BRAF/CRAF dimer formation (FIG. 1A). However, both drugs induced dimers between KSR and CRAF and enhanced dimer formation between KSR and BRAF (FIG. 1B/C). This suggested that KSR complexes induced by the drug might explain the positive effects of the BRAF inhibitors.

Example 2

This Example illustrates that BRAF inhibitor-induced ERK activation requires KSR.

In these experiments, we used KSR deficient cells (Nguyen, A., et al., Mol. Cell Biol. 22, 3035-3045, 2002) to determine whether KSR was required for the ability of the drugs to induce ERK activation. Cells transduced with constitutively active RAS (V12) or grown in serum were treated with various doses of each drug and activation was assessed by immunoblotting cell lysates with an antibody that detects active ERK. As reported previously, treatment of wild-type cells with either drug strongly induced ERK activation at low to intermediate doses but inhibited ERK activation at higher doses (Hatzivassiliou, G., et al., Nature 464, 431-435, 2010; Heidorn, S. J., et al., Cell 140, 209-221, 2010; Poulikakos, P. I., et al., Nature 464, 427-430, 2010) (FIG. 1D/E). Similar results were obtained with cells expressing constitutively active RAS (FIG. 1D/E) or after serum treatment (data not shown). Strikingly, ERK activation was almost undetectable in KSR deficient cells after drug treatment with either drug (FIG. 1D/E). FIG. 1D-E: Lysates, obtained from wild-type and KSR-deficient fibroblasts transfected with RasV12 and treated with the indicated doses of either GDC-0879 (FIG. 1D) or PLX4720 (FIG. 1E) for 1 hour, were immunoblotted for phospho-ERK1 and 2, ERK2 and RasV12.

Our data demonstrate that the ability of RAF inhibitors to activate ERK requires the presence of KSR. Given previous reports, demonstrating that CRAF and not BRAF is required for the positive effect of the drugs on ERK activation (Hatzivassiliou, G., et al., Nature 464, 431-435, 2010; Poulikakos, P. I., et al., Nature 464, 427-430, 2010), our data suggest that drug induced CRAF/KSR dimers may be the relevant complex.

Example 3

This example illustrates that KSR is a MEK kinase activated by CRAF.

In these experiments, we tested the function of the CRAF/KSR dimer by co-expressing both proteins and using PLX4720 (FIG. 1F) or GDC0879 (data not shown) to induce dimer formation between the two proteins. Because drug treatment is expected to induce activation of MEK and ERK, we treated cells with a saturating dose that would be expected to induce dimers but also inhibit CRAF activity. Under these conditions, we found that MEK was still activated suggesting that the presence of KSR might be effecting the function of the drugs (FIG. 1F). Importantly, a mutated form of CRAF (CRAF TM) that is unable to bind to the drug, did not result in phosphorylation of MEK. This result suggested that induction of the CRAF/KSR dimer might function to activate kinase activity towards MEK. FIG. 1F: KSR and CRAF cooperate to activate MEK. Cells expressing the indicated constructs were treated with a saturating dose of PLX for 2 hours before cell lysates were prepared and analyzed for pMEK by immunoblotting. CRAF(TM) refers to the T421M gatekeeper mutant that cannot bind to the drug (Heidorn, S. J., et al., Cell 140, 209-221, 2010).

We tested the possibility that KSR might have kinase activity by performing KSR in vitro kinase reactions. Consistent with previous reports, when KSR was expressed alone, we failed to detect KSR kinase activity in vitro against purified RAF (data not shown) or MEK (FIG. 1G). To test whether KSR might be activated by CRAF, we co-expressed KSR and CRAF and induced dimerization of CRAF with KSR by adding a low dose (10 μM) of PLX4720. KSR immunoprecipitates were then prepared and tested for kinase activity in vitro. To inhibit any contaminating RAF kinase activity co-precipitating with KSR, we preincubated the immunoprecipitates with an inhibitory dose of PLX4720 (50 μM). Treatment of cells with PLX4720 induced kinase activity towards MEK in the KSR immunoprecipitates and only occurred when KSR and CRAF were co-expressed together (FIG. 1G). This suggests that dimerization of KSR and CRAF activates KSR allowing it to phosphorylate MEK. FIG. 1G: KSR in vitro kinase reactions. Cells were co-transfected with WT or ATP binding deficient KSR and CRAF and immunoprecipitates prepared after cells were treated with an activating dose of PLX (10 μM) for one hour. Immunoprecipitates were prepared, pre-treated with 50 μM PLX to inhibit co-precipitating RAF activity and then tested for kinase activity using purified MEK. MEK phosphorylation was detected using a phospho-specific antibody that recognizes active MEK.

Example 4

This Example illustrates that ATP binding to KSR is required for its function.

Figure 2:
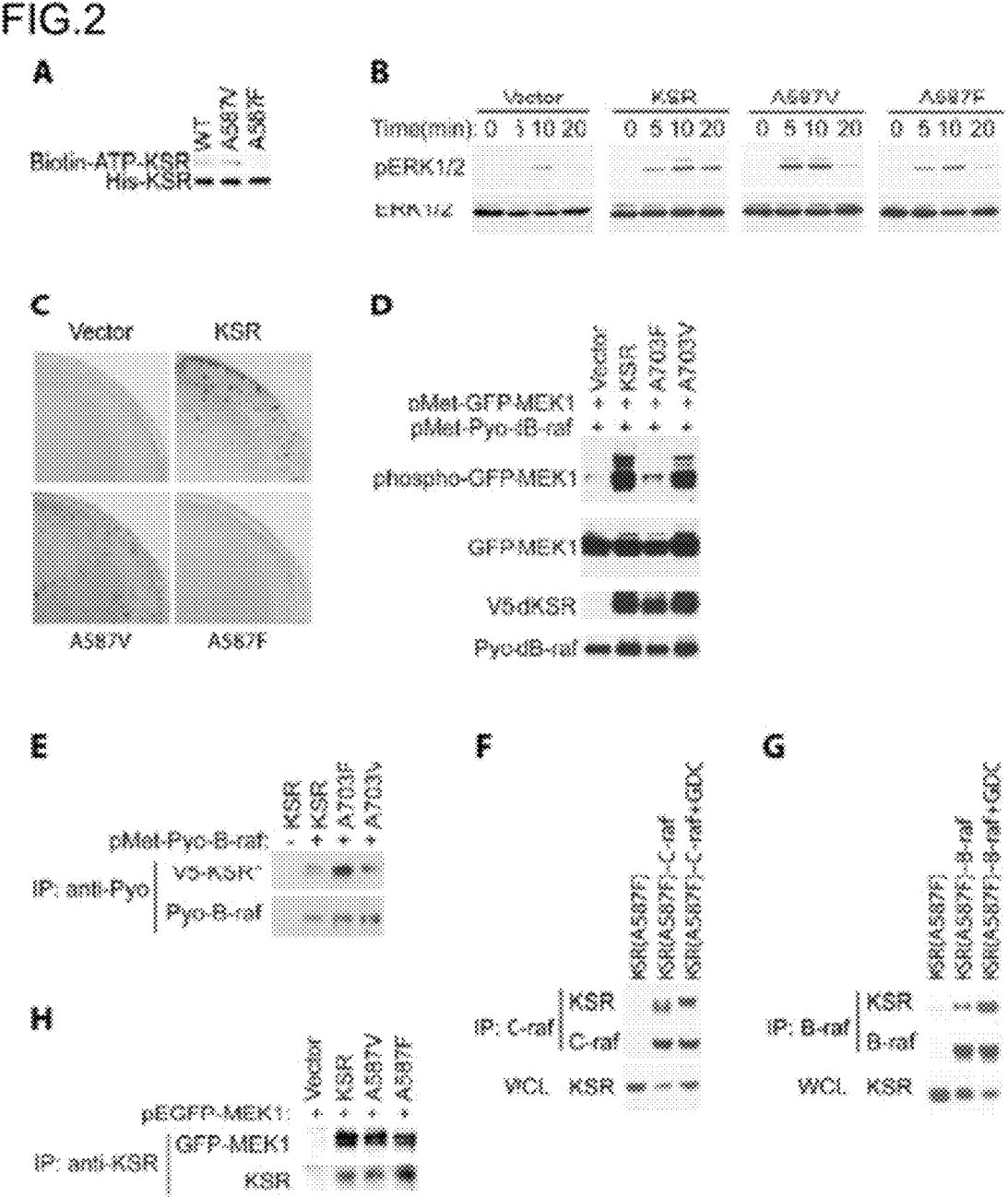
FIGS. 2A-H illustrate that the ability of KSR to bind ATP is required for the function of KSR.

In these experiments, to confirm the ability of KSR to function as a kinase, we were interested to generate a kinase-inactive mutant. Typically, substitution of the catalytic lysine with arginine or methionine can be used to ablate catalytic activity in most kinases (Gibbs, C. S., et al., J. Biol. Chem. 267, 4806-4814, 1992). Mammalian KSR lacks the catalytic lysine, partly explaining why it has always been considered to be an inactive pseudokinase. Recently several kinases lacking the catalytic lysine have been found to have kinase activity suggesting that new mutagenesis strategies might be needed to ablate kinase activity (Taylor, S. S. et al., Proc. Nat'l. Acad. Sci. USA 107, 8047-8048, 2010). Because mutations that disrupt catalytic activity still allow binding of ATP to the kinase (Iyer, G. H., et al., J. Mol. Biol. 351, 1110-1122, 2005), we sought to generate a KSR mutant that could not bind ATP and thus could not possess any catalytic activity. Based on the conserved structure of protein kinases, we reasoned that substituting the highly conserved alanine (A587) residue located in the back of the ATP binding pocket with a bulky hydrophobic residue might block ATP binding. Testing mutants for ATP binding using a biotin-ATP analog (FIG. 2A) demonstrated that substitution of A587 with phenylalanine, but not valine disrupted ATP binding. FIG. 2 illustrates that the ability of KSR to bind ATP is required for the function of KSR. FIG. 2A: mutagenesis was performed to substitute phenylalanine or valine for A587 of mouse 6× His-KSR1. Each mutant was expressed in cells, purified using $Ni^{2+}$ agarose and tested for ATP binding using a biotinylated-ATP analog after UV cross-linking and immunoblotting for the presence of biotin.

The function of the ATP binding deficient (A587F) KSR mutant was tested by reconstituting KSR deficient cells with either wild-type or one of the two KSR mutants, A587F or A587V. Because expression levels can affect the function of KSR, we used cell sorting of KSR-YFP fusion proteins to isolate stable cell lines with equivalent levels of KSR expression. EGF mediated ERK activation was then tested (FIG. 2B). While wild-type KSR and the ATP binding A587V mutant were both able to rescue ERK activation, the ATP binding deficient A587F mutant did not hilly rescue ERK activation in KSR deficient cell lines. FIG. 2B: KSR deficient fibroblasts were reconstituted with YFP-fused to wild-type or mutated KSR and sorted to generate cell lines with similar expression levels. Cells were stimulated with EGF for the indicated times and cell lysates were immunoblotted with an antibody to phosphorylated ERK (pERK).

We confirmed the inability of A587F to reconstitute KSR function using a Ras transformation assay (FIG. 2C). As cell transformation by RasV12 is dependent on KSR16, we transduced cell lines generated above with RasV12 and assessed cell transformation by focus-formation (FIG. 2C) or soft-agar assay (data not shown). While the wild-type and A587V mutants supported RasV12 transformation, the A587F mutant could not. Thus, replacement of alanine 587 of KSR with phenylalanine disrupts ATP binding and abrogates KSR function. FIG. 2C: Stably transfected KSR deficient cell lines, described in FIG. 2B, were transfected with an expression vector for RasV12 and assessed for transformed colony formation.

We confirmed this function of the mutants in Drosophila cells because overexpression of Drosophila KSR (dKSR) with Drosophila RAF (dRAF) is able to activate MEK by itself (Rajakulendran, T., et al., Nature 461, 542-545, 2009). We generated the analogous mutations in dKSR (A703V and A703F) and expressed them in Drosophila S2 cells with dRAF (FIG. 2D). Consistent with our previous results, the A703V mutant was still able to activate MEK while the A703F mutant had no effect. Lastly, we tested the KSR A587F mutant for kinase activity as described in FIG. 1G. In contrast to wild-type KSR that showed kinase activity towards MEK, no kinase activity was detected in KSR A587F immunoprecipitates. These results show that replacement of alanine 587 of KSR with phenylalanine disrupts ATP binding and that ATP binding is required for KSR function. FIG. 2D: Drosophila KSR mutant analogues were generated by site-directed mutagenesis, and coexpressed with Pyo-dBRAF and GFP-MEK in S2 cells. Cell lysates were immunoblotted for pMEK, GFP-MEK, V5-KSR and Pyo-dBRAF.

Example 5

This Example illustrates that KSR A587F mutant forms constitutive dimers with CRAF.

Kinases have two different functions, catalytic and scaffold. Since the scaffold function of KSR requires its ability to dimerize with RAF (McKay, M. M., Proc. Nat'l. Acad. Sci. USA 106, 11022-11027, 2009; Rajakulendran, T., et al., Nature 461, 542-545, 2009) and to bind MEK, we thus tested the KSR alanine to phenylalanine mutant for its ability to bind to RAF (FIG. 2 E/F/G) as well as to MEK (FIG. 2H). First, using the A703F mutant of dKSR to assess dimer formation between dKSR and dBRAF, we found, surprisingly, that dKSR/dBRAF dimers were promoted by the A703F mutation. To confirm whether this also occurred in mammalian KSR, we coexpressed the A587F KSR mutant with CRAF or BRAF and assessed dimer formation by co-immunoprecipitation (FIG. 2). While the A587F mutant now forms constitutive dimers with CRAF, it had little to no effect on dimer formation with BRAF (FIG. 2). The lack of any effect may be related to the high constitutive levels of KSR/BRAF dimers found in most cells. Lastly, the A587F mutation did not effect KSR binding to MEK (FIG. 2H). Thus, the two known scaffold functions of KSR are preserved. FIG. 2E: To access dimer formation, dBRAF immunoprecipitates were prepared from S2 cells that coexpressed dBRAF with either wild-type or mutated dKSR and immunoblotted for dKSR(V5) and dBRAF(pyo). FIG. 2F: Constitutive dimer formation between A587F KSR and CRAF. FLAG-KSR immunoprecipitates were prepared from lysates from cells expressing A587F FLAG-KSR with myc-CRAF and immunoblotted for CRAF (myc). FIG. 2G: No effect of A587F KSR mutation on binding to BRAF. Experiment was performed as described in F, except BRAF was used instead of CRAF. FIG. 2H: A587F KSR mutation does not effect MEK binding. KSR immunoprecipitates from cell co-expressing GFP-MEK1 and WT or KSR mutants were immunoblotted for GFP-MEK and KSR (FLAG).

Example 6

This Example illustrates that molecular modeling suggests that the A587F mutation induces the closed, active conformation of KSR.

The ability of the A587F mutant of KSR to induce constitutive dimer formation suggested that the phenylalanine substitution might be affecting the conformation of the kinase domain of KSR. A recent study of features conserved in the structures of active kinases and not present in the structures of inactive kinases suggests that kinase activation involves the formation of two hydrophobic spines, the catalytic and regulatory hydrophobic spines (Taylor, S. S. et al., Trends Biochem. Sci., 2010) (FIG. 3A). The formation of these two hydrophobic spines during the process of kinase activation serves to generate a hydrophobic core that stabilizes the active conformation of the kinase. In the catalytic hydrophobic spine of PKA, a conserved alanine (A70) from the upper lobe and a conserved leucine (L173) from the lower lobe interact with the top and bottom of the adenine ring from ATP to bring the two lobes of the kinase together. Alanine 587 of KSR corresponds to the conserved alanine residue from the upper lobe and the leucine in the lower lobe (173 of PKA) corresponds to phenylalanine (690) of KSR.

We first analyzed the published structure of CRAF bound to GDC08792, a Type I inhibitor, and confirmed that drug binding induced the formation of both the catalytic and regulatory spines (FIG. 3). In contrast, analysis of a structure of BRAF complexed with Sorafenib (Wan, P. T., et al. Cell 116, 855-867, 2004), a Type II inhibitor, was consistent with an inactive kinase without assembly of the hydrophobic spines (FIG. 3). Using energy minimization modeling, the structure of CRAF with alanine replaced by phenylalanine was modeled. The results showed that the phenylalanine residue in CRAF position 573 can complete the catalytic hydrophobic spine by interacting with phenylalanine 690 in the lower lobe. This interaction induces the closed, active conformation of the kinase (FIG. 3). This model suggested that the A587F mutant of KSR mimics ATP binding resulting truly in a pseudokinase that is conformationally active but catalytically inert because it can no longer bind to ATP.

FIG. 3 illustrates modeling the structural effects of the alanine to phenylalanine change in CRAF and BRAF. The position of residues constituting the hydrophobic spines of CRAF crystallized with a Type I inhibitor (stabilizes the closed and ATP bound form of the kinase) are shown in FIG. 3A while the hydrophobic spine residues in BRAF bound to a Type II inhibitor (binds to the open conformation preventing closing of the cleft) is shown in FIG. 3B. Components of the catalytic hydrophobic spine are indicated by thin arrows while components of the regulatory hydrophobic spine are indicated by thick arrows. Note the contiguous residues of induced by the Type I inhibitor indicated by asterisk in FIG. 3A while the pattern of these residues is interrupted in FIG. 3B, in which the inhibitor is also indicated by an asterisk. Note also how the drug molecule in FIG. 3A functions to connect components of the catalytic hydrophobic spine in the upper and lower lobes of the kinase. In FIG. 3C, a simulated structure of CRAF where A373 is replaced with Phe is shown. Energy minimization was done using the program TINKER.

Example 7

This Example illustrates that Analogous A to F mutations in BRAF and CRAF induce dimer formation.

In these experiments, to test the generality of this hypothesis, we generated analogous mutations in BRAF and CRAF. Co-immunoprecipitation assays showed that BRAF A481 F formed constitutive dimers with CRAF and that CR AF A373F formed constitutive dimers with BRAF (FIG. 4A). The CRAF A373F mutant also formed constitutive dimers with KSR but the BRAF A481 F did not enhance basal dimer formation with KSR (FIG. 4B).

Since the AF mutants appear to induce the closed, active conformation of all three kinases, we reasoned that we could use these mutants to distinguish between their functions as enzymes or as scaffolds. All three AF mutants (BRAF, CRAF and KSR) were over-expressed in cells and tested for their effects on endogenous ERK activation (FIG. 4C). Consistent with previous work showing that kinase-inactive forms of BRAF can stimulate the activation of MEK and ERK, over-expression of the BRAF A481 F mutant resulted in constitutive activation of ERK. However, co-expression of a dominant negative RAS (N17), showed that its ability to activate ERK was RAS independent (FIG. 4C). The ability of kinase dead BRAFs to activate ERK usually requires RAS activation (Heidorn, S. J., et al., Cell 140, 209-221, 2010; Wan, P. T., et al. Cell 116, 855-867, 2004) presumably because this is required to induce the active conformation of BRAF by releasing the inhibitory N-terminal domain. The RAS independence of A481 F BRAF supports the idea that the phenylalanine mutation is sufficient to induce the active conformation of the kinase domain but also results in displacement of the inhibitory N-terminal domain. The RAS independence of A481 F BRAF thus resembles the V600E mutant of BRAF and suggests provocatively that the greatly increased kinase activity of BRAF V600E need not be the only reason it is oncogenic. Rather, the scaffold function and not its kinase activity of BRAF is required.

We tested whether ERK activation by BRAF A481 F or BRAF V600E required KSR by expressing each construct in the KSR deficient cell line (FIG. 4D/E). The ability of both proteins to activate ERK was significantly compromised in the absence of KSR. This supports the idea that the mechanism of function of both A481 F and V600E are similar and dependent on the presence of KSR. In contrast, overexpression of CRAF A373F or KSR A587F had no constitutive effects on ERK activation (FIG. 4C). As both mutants form constitutive dimers with each other, and as shown above (FIG. 2), dimerization induces MEK phosphorylation, these results suggest that both proteins need to be enzymatically active.

FIG. 4 illustrates that an A to F mutation in RAF can induce dimer formation and activate ERK signaling. FIG. 4A illustrates that phenylalanine substitutions in CRAF and BRAF allow for constitutive CRAF/BRAF dimers. The myc-CRAF A373F and the BRAF A481 F mutants were co-expressed with wild-type BRAF or wild-type myc-CRAF respectively and heterodimers assessed by co-immunoprecipitation. FIG. 4B illustrates that CRAF but not the BRAF phenylalanine substitution allows enhanced KSR dimer formation. In these experiments, the myc-CRAF A373F and the BRAF A481 F mutants were co-expressed with wild-type FLAG-KSR and heterodimers assessed by co-immunoprecipitations. FIG. 4C illustrates that expression of BRAF A481 F stimulates Ras independent ERK activation in cells. In these experiments, cells were transiently transfected with expression constructs for BRAF A481 F, myc-CRAF A373F or FLAG-KSR A587F mutants. Lysates were immunoblotted with antibodies to pERK after 18 hours. The effect of BRAF A481 F was not inhibited by co-expression of dominant negative Ras (N17). FIG. 4D illustrates ERK phosphorylation. In these experiments, WT and ksr$^{-/-}$ MEFs were transfected with BRAF (A481 F). 24 hours later, cells were treated with or without 20 uM GDC0879 for 60 min, before lysis. ERK phosphorylation was assessed by immunoblotting. Immunoblotting for total ERK2 was used as a loading control. FIG. 4E illustrates WT and ksr$^{-/-}$ MEFs transfected with BRAF(V600E) and prepared as described in FIG. 4D.

Example 8

This example illustrates an in vitro kinase assay that can be used to identify an inhibitor of KSR.

HeLa cells can be transiently transfected with expression constructs for FLAG-KSR L591F. Cells can be treated with a candidate inhibitor of KSR kinase activity for 60 min before lysis. Cells then can be lysed with buffer containing 20 mM HEPES (pH 7.5). 50 mM GP, 100 M sodium vanadate, 2 mM magnesium chloride, 1 mM EGTA, 0.5% Triton X-100, 5 g/ml leupeptin, 21 g/ml aprotinin and 1 mM DTT. Protein concentration can be determined using the method of Bradford and KSR can be immunoprecipitated from 400 g of cell lysate with an anti-FLAG antibody. Immunoprecipitates can be washed and in vitro kinase assays can be carried out at 30° C. for 20 min in buffer containing 20 mM HEPES (pH 7.5), 50 mM β-glycerophosphate, 100 μM sodium vanadate, 20 mM magnesium chloride, 0.1 mM EGTA, 0.2 mM ATP, 10 μCi [γ-$^{32}$P]ATP (ICN Biologicals), 50 μg/ml IP-20 peptide and 80 μM of MEK peptide as a selective substrate for KSR L591F activity. The kinase reaction can be terminated by the addition of SDS sample buffer (0.31 M Tris pH 6.8, 11.5% SDS, 50 mM DTT, 50% glycerol), samples can be boiled, and then size fractionated by SDS-PAGE, and 32P-labeled MEK can be visualized by autoradiography. PhosphorImager analysis can be utilized to quantify the relative differences in MEK phosphorylation as a measure of KSR L591F activity in the absence or presence of an inhibitor.

As used in the description and the appended claims, the singular forms "a", "an" and "the" are intended to include the plural forms as well, unless the context indicates otherwise.

All publications, patent applications, patents, and other references mentioned herein are incorporated by reference in their entirety.

What is claimed is:

1. A polypeptide comprising the mutant pseudokinase set forth by the amino acid sequence of SEQ NO: 8.

2. The polypeptide of claim 1 consisting of the mutant pseudokinase set forth by the amino acid sequence of SEQ NO: 8.

* * * * *

SEQUENCE LISTING

```
<160> NUMBER OF SEQ ID NOS: 10

<210> SEQ ID NO 1
<211> LENGTH: 762
<212> TYPE: PRT
<213> ORGANISM: Homo sapiens

<400> SEQUENCE: 1

Met Asn Glu Ala Lys Val Lys Glu Thr Leu Arg Arg Cys Gly Ala Ser
1               5                   10                  15

Gly Asp Glu Cys Gly Arg Leu Gln Tyr Ala Leu Thr Cys Leu Arg Lys
            20                  25                  30

Val Thr Gly Leu Gly Gly Glu His Lys Glu Asp Ser Ser Trp Ser Ser
        35                  40                  45

Leu Asp Ala Arg Arg Glu Ser Gly Ser Gly Pro Ser Thr Asp Thr Leu
    50                  55                  60

Ser Ala Ala Ser Leu Pro Trp Pro Pro Gly Ser Ser Gln Leu Gly Arg
65                  70                  75                  80

Ala Gly Asn Ser Ala Gln Gly Pro Arg Ser Ile Ser Val Ser Ala Leu
                85                  90                  95

Pro Ala Ser Asp Ser Pro Thr Pro Ser Phe Ser Glu Gly Leu Ser Asp
            100                 105                 110

Thr Cys Ile Pro Leu His Ala Ser Gly Arg Leu Thr Pro Arg Ala Leu
        115                 120                 125

His Ser Phe Ile Thr Pro Pro Thr Thr Pro Gln Leu Arg Arg His Thr
    130                 135                 140

Lys Leu Lys Pro Pro Arg Thr Pro Pro Pro Ser Arg Lys Val Phe
145                 150                 155                 160

Gln Leu Leu Pro Ser Phe Pro Thr Leu Thr Arg Ser Lys Ser His Glu
                165                 170                 175

Ser Gln Leu Gly Asn Arg Ile Asp Asp Val Ser Ser Met Arg Phe Asp
            180                 185                 190

Leu Ser His Gly Ser Pro Gln Met Val Arg Arg Asp Ile Gly Leu Ser
        195                 200                 205
```

```
Val Thr His Arg Phe Ser Thr Lys Ser Trp Leu Ser Gln Val Cys His
    210                 215                 220
Val Cys Gln Lys Ser Met Ile Phe Gly Val Lys Cys Lys His Cys Arg
225                 230                 235                 240
Leu Lys Cys His Asn Lys Cys Thr Lys Glu Ala Pro Ala Cys Arg Ile
                245                 250                 255
Ser Phe Leu Pro Leu Thr Arg Leu Arg Arg Thr Glu Ser Val Pro Ser
            260                 265                 270
Asp Ile Asn Asn Pro Val Asp Arg Ala Ala Glu Pro His Phe Gly Thr
        275                 280                 285
Leu Pro Lys Ala Leu Thr Lys Lys Glu His Pro Pro Ala Met Asn His
    290                 295                 300
Leu Asp Ser Ser Ser Asn Pro Ser Ser Thr Thr Ser Ser Thr Pro Ser
305                 310                 315                 320
Ser Pro Ala Pro Phe Pro Thr Ser Ser Asn Pro Ser Ser Ala Thr Thr
                325                 330                 335
Pro Pro Asn Pro Ser Pro Gly Gln Arg Asp Ser Arg Phe Asn Phe Pro
            340                 345                 350
Ala Ala Tyr Phe Ile His His Arg Gln Gln Phe Ile Phe Pro Val Pro
        355                 360                 365
Ser Ala Gly His Cys Trp Lys Cys Leu Leu Ile Ala Glu Ser Leu Lys
    370                 375                 380
Glu Asn Ala Phe Asn Ile Ser Ala Phe Ala His Ala Ala Pro Leu Pro
385                 390                 395                 400
Glu Ala Ala Asp Gly Thr Arg Leu Asp Asp Gln Pro Lys Ala Asp Val
                405                 410                 415
Leu Glu Ala His Glu Ala Glu Ala Glu Glu Pro Glu Ala Gly Lys Ser
            420                 425                 430
Glu Ala Glu Asp Asp Glu Asp Glu Val Asp Asp Leu Pro Ser Ser Arg
        435                 440                 445
Arg Pro Trp Arg Gly Pro Ile Ser Arg Lys Ala Ser Gln Thr Ser Val
    450                 455                 460
Tyr Leu Gln Glu Trp Asp Ile Pro Phe Glu Gln Val Glu Leu Gly Glu
465                 470                 475                 480
Pro Ile Gly Gln Gly Arg Trp Gly Arg Val His Arg Gly Arg Trp His
                485                 490                 495
Gly Glu Val Ala Ile Arg Leu Leu Glu Met Asp Gly His Asn Gln Asp
            500                 505                 510
His Leu Lys Leu Phe Lys Lys Glu Val Met Asn Tyr Arg Gln Thr Arg
    515                 520                 525
His Glu Asn Val Val Leu Phe Met Gly Ala Cys Met Asn Pro Pro His
530                 535                 540
Leu Ala Ile Ile Thr Ser Phe Cys Lys Gly Arg Thr Leu His Ser Phe
545                 550                 555                 560
Val Arg Asp Pro Lys Thr Ser Leu Asp Ile Asn Lys Thr Arg Gln Ile
                565                 570                 575
Ala Gln Glu Ile Ile Lys Gly Met Gly Tyr Leu His Ala Lys Gly Ile
            580                 585                 590
Val His Lys Asp Leu Lys Ser Lys Asn Val Phe Tyr Asp Asn Gly Lys
        595                 600                 605
Val Val Ile Thr Asp Phe Gly Leu Phe Gly Ile Ser Gly Val Val Arg
    610                 615                 620
```

-continued

```
Glu Gly Arg Arg Glu Asn Gln Leu Lys Leu Ser His Asp Trp Leu Cys
625                 630                 635                 640

Tyr Leu Ala Pro Glu Ile Val Arg Glu Met Thr Pro Gly Lys Asp Glu
            645                 650                 655

Asp Gln Leu Pro Phe Ser Lys Ala Ala Asp Val Tyr Ala Phe Gly Thr
        660                 665                 670

Val Trp Tyr Glu Leu Gln Ala Arg Asp Trp Pro Leu Lys Asn Gln Ala
    675                 680                 685

Ala Glu Ala Ser Ile Trp Gln Ile Gly Ser Gly Glu Gly Met Lys Arg
690                 695                 700

Val Leu Thr Ser Val Ser Leu Gly Lys Glu Val Ser Glu Ile Leu Ser
705                 710                 715                 720

Ala Cys Trp Ala Phe Asp Leu Gln Glu Arg Pro Ser Phe Ser Leu Leu
            725                 730                 735

Met Asp Met Leu Glu Lys Leu Pro Lys Leu Asn Arg Arg Leu Ser His
        740                 745                 750

Pro Gly His Phe Trp Lys Ser Ala Glu Leu
    755                 760

<210> SEQ ID NO 2
<211> LENGTH: 762
<212> TYPE: PRT
<213> ORGANISM: Homo sapiens

<400> SEQUENCE: 2

Met Asn Glu Ala Lys Val Lys Glu Thr Leu Arg Arg Cys Gly Ala Ser
1               5                   10                  15

Gly Asp Glu Cys Gly Arg Leu Gln Tyr Ala Leu Thr Cys Leu Arg Lys
            20                  25                  30

Val Thr Gly Leu Gly Gly Glu His Lys Glu Asp Ser Ser Trp Ser Ser
        35                  40                  45

Leu Asp Ala Arg Arg Glu Ser Gly Ser Gly Pro Ser Thr Asp Thr Leu
    50                  55                  60

Ser Ala Ala Ser Leu Pro Trp Pro Pro Gly Ser Ser Gln Leu Gly Arg
65                  70                  75                  80

Ala Gly Asn Ser Ala Gln Gly Pro Arg Ser Ile Ser Val Ser Ala Leu
                85                  90                  95

Pro Ala Ser Asp Ser Pro Thr Pro Ser Phe Ser Glu Gly Leu Ser Asp
            100                 105                 110

Thr Cys Ile Pro Leu His Ala Ser Gly Arg Leu Thr Pro Arg Ala Leu
        115                 120                 125

His Ser Phe Ile Thr Pro Pro Thr Thr Pro Gln Leu Arg Arg His Thr
    130                 135                 140

Lys Leu Lys Pro Pro Arg Thr Pro Pro Pro Ser Arg Lys Val Phe
145                 150                 155                 160

Gln Leu Leu Pro Ser Phe Pro Thr Leu Thr Arg Ser Lys Ser His Glu
                165                 170                 175

Ser Gln Leu Gly Asn Arg Ile Asp Asp Val Ser Ser Met Arg Phe Asp
            180                 185                 190

Leu Ser His Gly Ser Pro Gln Met Val Arg Arg Asp Ile Gly Leu Ser
        195                 200                 205

Val Thr His Arg Phe Ser Thr Lys Ser Trp Leu Ser Gln Val Cys His
    210                 215                 220

Val Cys Gln Lys Ser Met Ile Phe Gly Val Lys Cys Lys His Cys Arg
225                 230                 235                 240
```

```
Leu Lys Cys His Asn Lys Cys Thr Lys Glu Ala Pro Ala Cys Arg Ile
            245                 250                 255

Ser Phe Leu Pro Leu Thr Arg Leu Arg Arg Thr Glu Ser Val Pro Ser
        260                 265                 270

Asp Ile Asn Asn Pro Val Asp Arg Ala Ala Glu Pro His Phe Gly Thr
        275                 280                 285

Leu Pro Lys Ala Leu Thr Lys Lys Glu His Pro Pro Ala Met Asn His
    290                 295                 300

Leu Asp Ser Ser Asn Pro Ser Ser Thr Thr Ser Ser Thr Pro Ser
305                 310                 315                 320

Ser Pro Ala Pro Phe Pro Thr Ser Ser Asn Pro Ser Ser Ala Thr Thr
                325                 330                 335

Pro Pro Asn Pro Ser Pro Gly Gln Arg Asp Ser Arg Phe Asn Phe Pro
            340                 345                 350

Ala Ala Tyr Phe Ile His His Arg Gln Gln Phe Ile Phe Pro Val Pro
        355                 360                 365

Ser Ala Gly His Cys Trp Lys Cys Leu Leu Ile Ala Glu Ser Leu Lys
        370                 375                 380

Glu Asn Ala Phe Asn Ile Ser Ala Phe Ala His Ala Ala Pro Leu Pro
385                 390                 395                 400

Glu Ala Ala Asp Gly Thr Arg Leu Asp Asp Gln Pro Lys Ala Asp Val
                405                 410                 415

Leu Glu Ala His Glu Ala Glu Ala Glu Pro Glu Ala Gly Lys Ser
                420                 425                 430

Glu Ala Glu Asp Asp Glu Asp Glu Val Asp Asp Leu Pro Ser Ser Arg
            435                 440                 445

Arg Pro Trp Arg Gly Pro Ile Ser Arg Lys Ala Ser Gln Thr Ser Val
        450                 455                 460

Tyr Leu Gln Glu Trp Asp Ile Pro Phe Glu Gln Val Glu Leu Gly Glu
465                 470                 475                 480

Pro Ile Gly Gln Gly Arg Trp Gly Arg Val His Arg Gly Arg Trp His
                485                 490                 495

Gly Glu Val Phe Ile Arg Leu Leu Glu Met Asp Gly His Asn Gln Asp
            500                 505                 510

His Leu Lys Leu Phe Lys Lys Glu Val Met Asn Tyr Arg Gln Thr Arg
        515                 520                 525

His Glu Asn Val Val Leu Phe Met Gly Ala Cys Met Asn Pro Pro His
        530                 535                 540

Leu Ala Ile Ile Thr Ser Phe Cys Lys Gly Arg Thr Leu His Ser Phe
545                 550                 555                 560

Val Arg Asp Pro Lys Thr Ser Leu Asp Ile Asn Lys Thr Arg Gln Ile
                565                 570                 575

Ala Gln Glu Ile Ile Lys Gly Met Gly Tyr Leu His Ala Lys Gly Ile
            580                 585                 590

Val His Lys Asp Leu Lys Ser Lys Asn Val Phe Tyr Asp Asn Gly Lys
        595                 600                 605

Val Val Ile Thr Asp Phe Gly Leu Phe Gly Ile Ser Gly Val Val Arg
        610                 615                 620

Glu Gly Arg Arg Glu Asn Gln Leu Lys Leu Ser His Asp Trp Leu Cys
625                 630                 635                 640

Tyr Leu Ala Pro Glu Ile Val Arg Glu Met Thr Pro Gly Lys Asp Glu
                645                 650                 655
```

```
Asp Gln Leu Pro Phe Ser Lys Ala Ala Asp Val Tyr Ala Phe Gly Thr
            660                 665                 670

Val Trp Tyr Glu Leu Gln Ala Arg Asp Trp Pro Leu Lys Asn Gln Ala
        675                 680                 685

Ala Glu Ala Ser Ile Trp Gln Ile Gly Ser Gly Glu Gly Met Lys Arg
    690                 695                 700

Val Leu Thr Ser Val Ser Leu Gly Lys Glu Val Ser Glu Ile Leu Ser
705                 710                 715                 720

Ala Cys Trp Ala Phe Asp Leu Gln Glu Arg Pro Ser Phe Ser Leu Leu
                725                 730                 735

Met Asp Met Leu Glu Lys Leu Pro Lys Leu Asn Arg Arg Leu Ser His
            740                 745                 750

Pro Gly His Phe Trp Lys Ser Ala Glu Leu
        755                 760

<210> SEQ ID NO 3
<211> LENGTH: 766
<212> TYPE: PRT
<213> ORGANISM: Homo sapiens

<400> SEQUENCE: 3

Met Ala Ala Leu Ser Gly Gly Gly Gly Gly Gly Ala Glu Pro Gly Gln
1               5                   10                  15

Ala Leu Phe Asn Gly Asp Met Glu Pro Glu Ala Gly Ala Gly Ala Gly
            20                  25                  30

Ala Ala Ala Ser Ser Ala Ala Asp Pro Ala Ile Pro Glu Glu Val Trp
        35                  40                  45

Asn Ile Lys Gln Met Ile Lys Leu Thr Gln Glu His Ile Glu Ala Leu
50                  55                  60

Leu Asp Lys Phe Gly Gly Glu His Asn Pro Pro Ser Ile Tyr Leu Glu
65                  70                  75                  80

Ala Tyr Glu Glu Tyr Thr Ser Lys Leu Asp Ala Leu Gln Gln Arg Glu
                85                  90                  95

Gln Gln Leu Leu Glu Ser Leu Gly Asn Gly Thr Asp Phe Ser Val Ser
            100                 105                 110

Ser Ser Ala Ser Met Asp Thr Val Thr Ser Ser Ser Ser Ser Ser Leu
        115                 120                 125

Ser Val Leu Pro Ser Ser Leu Ser Val Phe Gln Asn Pro Thr Asp Val
130                 135                 140

Ala Arg Ser Asn Pro Lys Ser Pro Gln Lys Pro Ile Val Arg Val Phe
145                 150                 155                 160

Leu Pro Asn Lys Gln Arg Thr Val Val Pro Ala Arg Cys Gly Val Thr
                165                 170                 175

Val Arg Asp Ser Leu Lys Lys Ala Leu Met Met Arg Gly Leu Ile Pro
            180                 185                 190

Glu Cys Cys Ala Val Tyr Arg Ile Gln Asp Gly Glu Lys Lys Pro Ile
        195                 200                 205

Gly Trp Asp Thr Asp Ile Ser Trp Leu Thr Gly Glu Glu Leu His Val
210                 215                 220

Glu Val Leu Glu Asn Val Pro Leu Thr Thr His Asn Phe Val Arg Lys
225                 230                 235                 240

Thr Phe Phe Thr Leu Ala Phe Cys Asp Phe Cys Arg Lys Leu Leu Phe
                245                 250                 255

Gln Gly Phe Arg Cys Gln Thr Cys Gly Tyr Lys Phe His Gln Arg Cys
            260                 265                 270
```

```
Ser Thr Glu Val Pro Leu Met Cys Val Asn Tyr Asp Gln Leu Asp Leu
        275                 280                 285

Leu Phe Val Ser Lys Phe Phe Glu His His Pro Ile Pro Gln Glu Glu
290                 295                 300

Ala Ser Leu Ala Glu Thr Ala Leu Thr Ser Gly Ser Ser Pro Ser Ala
305                 310                 315                 320

Pro Ala Ser Asp Ser Ile Gly Pro Gln Ile Leu Thr Ser Pro Ser Pro
                325                 330                 335

Ser Lys Ser Ile Pro Ile Pro Gln Pro Phe Arg Pro Ala Asp Glu Asp
                340                 345                 350

His Arg Asn Gln Phe Gly Gln Arg Asp Arg Ser Ser Ala Pro Asn
                355                 360                 365

Val His Ile Asn Thr Ile Glu Pro Val Asn Ile Asp Asp Leu Ile Arg
370                 375                 380

Asp Gln Gly Phe Arg Gly Asp Gly Ser Thr Thr Gly Leu Ser Ala
385                 390                 395                 400

Thr Pro Pro Ala Ser Leu Pro Gly Ser Leu Thr Asn Val Lys Ala Leu
                405                 410                 415

Gln Lys Ser Pro Gly Pro Gln Arg Glu Arg Lys Ser Ser Ser Ser
                420                 425                 430

Glu Asp Arg Asn Arg Met Lys Thr Leu Gly Arg Arg Asp Ser Ser Asp
                435                 440                 445

Asp Trp Glu Ile Pro Asp Gly Gln Ile Thr Val Gly Gln Arg Ile Gly
        450                 455                 460

Ser Gly Ser Phe Gly Thr Val Tyr Lys Gly Lys Trp His Gly Asp Val
465                 470                 475                 480

Ala Val Lys Met Leu Asn Val Thr Ala Pro Thr Pro Gln Gln Leu Gln
                485                 490                 495

Ala Phe Lys Asn Glu Val Gly Val Leu Arg Lys Thr Arg His Val Asn
                500                 505                 510

Ile Leu Leu Phe Met Gly Tyr Ser Thr Lys Pro Gln Leu Ala Ile Val
                515                 520                 525

Thr Gln Trp Cys Glu Gly Ser Ser Leu Tyr His His Leu His Ile Ile
        530                 535                 540

Glu Thr Lys Phe Glu Met Ile Lys Leu Ile Asp Ile Ala Arg Gln Thr
545                 550                 555                 560

Ala Gln Gly Met Asp Tyr Leu His Ala Lys Ser Ile Ile His Arg Asp
                565                 570                 575

Leu Lys Ser Asn Asn Ile Phe Leu His Glu Asp Leu Thr Val Lys Ile
                580                 585                 590

Gly Asp Phe Gly Leu Ala Thr Val Lys Ser Arg Trp Ser Gly Ser His
        595                 600                 605

Gln Phe Glu Gln Leu Ser Gly Ser Ile Leu Trp Met Ala Pro Glu Val
        610                 615                 620

Ile Arg Met Gln Asp Lys Asn Pro Tyr Ser Phe Gln Ser Asp Val Tyr
625                 630                 635                 640

Ala Phe Gly Ile Val Leu Tyr Glu Leu Met Thr Gly Gln Leu Pro Tyr
                645                 650                 655

Ser Asn Ile Asn Asn Arg Asp Gln Ile Ile Phe Met Val Gly Arg Gly
                660                 665                 670

Tyr Leu Ser Pro Asp Leu Ser Lys Val Arg Ser Asn Cys Pro Lys Ala
                675                 680                 685
```

```
Met Lys Arg Leu Met Ala Glu Cys Leu Lys Lys Lys Arg Asp Glu Arg
    690             695                 700
Pro Leu Phe Pro Gln Ile Leu Ala Ser Ile Glu Leu Leu Ala Arg Ser
705             710                 715                 720
Leu Pro Lys Ile His Arg Ser Ala Ser Glu Pro Ser Leu Asn Arg Ala
                725                 730                 735
Gly Phe Gln Thr Glu Asp Phe Ser Leu Tyr Ala Cys Ala Ser Pro Lys
                740                 745                 750
Thr Pro Ile Gln Ala Gly Gly Tyr Gly Ala Phe Pro Val His
                755                 760                 765
```

<210> SEQ ID NO 4
<211> LENGTH: 766
<212> TYPE: PRT
<213> ORGANISM: Homo sapiens

<400> SEQUENCE: 4

```
Met Ala Ala Leu Ser Gly Gly Gly Gly Gly Ala Glu Pro Gly Gln
1               5                   10                  15
Ala Leu Phe Asn Gly Asp Met Glu Pro Glu Ala Gly Ala Gly Ala Gly
                20                  25                  30
Ala Ala Ala Ser Ser Ala Ala Asp Pro Ala Ile Pro Glu Glu Val Trp
                35                  40                  45
Asn Ile Lys Gln Met Ile Lys Leu Thr Gln Glu His Ile Glu Ala Leu
50                  55                  60
Leu Asp Lys Phe Gly Gly Glu His Asn Pro Pro Ser Ile Tyr Leu Glu
65                  70                  75                  80
Ala Tyr Glu Glu Tyr Thr Ser Lys Leu Asp Ala Leu Gln Gln Arg Glu
                85                  90                  95
Gln Gln Leu Leu Glu Ser Leu Gly Asn Gly Thr Asp Phe Ser Val Ser
                100                 105                 110
Ser Ser Ala Ser Met Asp Thr Val Thr Ser Ser Ser Ser Ser Ser Leu
                115                 120                 125
Ser Val Leu Pro Ser Ser Leu Ser Val Phe Gln Asn Pro Thr Asp Val
130                 135                 140
Ala Arg Ser Asn Pro Lys Ser Pro Gln Lys Pro Ile Val Arg Val Phe
145                 150                 155                 160
Leu Pro Asn Lys Gln Arg Thr Val Val Pro Ala Arg Cys Gly Val Thr
                165                 170                 175
Val Arg Asp Ser Leu Lys Lys Ala Leu Met Met Arg Gly Leu Ile Pro
                180                 185                 190
Glu Cys Cys Ala Val Tyr Arg Ile Gln Asp Gly Glu Lys Lys Pro Ile
                195                 200                 205
Gly Trp Asp Thr Asp Ile Ser Trp Leu Thr Gly Glu Glu Leu His Val
                210                 215                 220
Glu Val Leu Glu Asn Val Pro Leu Thr Thr His Asn Phe Val Arg Lys
225                 230                 235                 240
Thr Phe Phe Thr Leu Ala Phe Cys Asp Phe Cys Arg Lys Leu Leu Phe
                245                 250                 255
Gln Gly Phe Arg Cys Gln Thr Cys Gly Tyr Lys Phe His Gln Arg Cys
                260                 265                 270
Ser Thr Glu Val Pro Leu Met Cys Val Asn Tyr Asp Gln Leu Asp Leu
                275                 280                 285
Leu Phe Val Ser Lys Phe Phe Glu His His Pro Ile Pro Gln Glu Glu
                290                 295                 300
```

```
Ala Ser Leu Ala Glu Thr Ala Leu Thr Ser Gly Ser Pro Ser Ala
305                 310                 315                 320

Pro Ala Ser Asp Ser Ile Gly Pro Gln Ile Leu Thr Ser Pro Ser Pro
            325                 330                 335

Ser Lys Ser Ile Pro Ile Pro Gln Pro Phe Arg Pro Ala Asp Glu Asp
        340                 345                 350

His Arg Asn Gln Phe Gly Gln Arg Asp Arg Ser Ser Ala Pro Asn
            355                 360                 365

Val His Ile Asn Thr Ile Glu Pro Val Asn Ile Asp Asp Leu Ile Arg
370                 375                 380

Asp Gln Gly Phe Arg Gly Asp Gly Gly Ser Thr Thr Gly Leu Ser Ala
385                 390                 395                 400

Thr Pro Pro Ala Ser Leu Pro Gly Ser Leu Thr Asn Val Lys Ala Leu
                405                 410                 415

Gln Lys Ser Pro Gly Pro Gln Arg Glu Arg Lys Ser Ser Ser Ser
            420                 425                 430

Glu Asp Arg Asn Arg Met Lys Thr Leu Gly Arg Arg Asp Ser Ser Asp
            435                 440                 445

Asp Trp Glu Ile Pro Asp Gly Gln Ile Thr Val Gly Gln Arg Ile Gly
450                 455                 460

Ser Gly Ser Phe Gly Thr Val Tyr Lys Gly Lys Trp His Gly Asp Val
465                 470                 475                 480

Phe Val Lys Met Leu Asn Val Thr Ala Pro Thr Pro Gln Gln Leu Gln
                485                 490                 495

Ala Phe Lys Asn Glu Val Gly Val Leu Arg Lys Thr Arg His Val Asn
                500                 505                 510

Ile Leu Leu Phe Met Gly Tyr Ser Thr Lys Pro Gln Leu Ala Ile Val
            515                 520                 525

Thr Gln Trp Cys Glu Gly Ser Ser Leu Tyr His His Leu His Ile Ile
            530                 535                 540

Glu Thr Lys Phe Glu Met Ile Lys Leu Ile Asp Ile Ala Arg Gln Thr
545                 550                 555                 560

Ala Gln Gly Met Asp Tyr Leu His Ala Lys Ser Ile Ile His Arg Asp
                565                 570                 575

Leu Lys Ser Asn Asn Ile Phe Leu His Glu Asp Leu Thr Val Lys Ile
            580                 585                 590

Gly Asp Phe Gly Leu Ala Thr Val Lys Ser Arg Trp Ser Gly Ser His
            595                 600                 605

Gln Phe Glu Gln Leu Ser Gly Ser Ile Leu Trp Met Ala Pro Glu Val
            610                 615                 620

Ile Arg Met Gln Asp Lys Asn Pro Tyr Ser Phe Gln Ser Asp Val Tyr
625                 630                 635                 640

Ala Phe Gly Ile Val Leu Tyr Glu Leu Met Thr Gly Gln Leu Pro Tyr
                645                 650                 655

Ser Asn Ile Asn Asn Arg Asp Gln Ile Ile Phe Met Val Gly Arg Gly
            660                 665                 670

Tyr Leu Ser Pro Asp Leu Ser Lys Val Arg Ser Asn Cys Pro Lys Ala
            675                 680                 685

Met Lys Arg Leu Met Ala Glu Cys Leu Lys Lys Lys Arg Asp Glu Arg
            690                 695                 700

Pro Leu Phe Pro Gln Ile Leu Ala Ser Ile Glu Leu Leu Ala Arg Ser
705                 710                 715                 720
```

```
Leu Pro Lys Ile His Arg Ser Ala Ser Glu Pro Ser Leu Asn Arg Ala
                725                 730                 735
Gly Phe Gln Thr Glu Asp Phe Ser Leu Tyr Ala Cys Ala Ser Pro Lys
            740                 745                 750
Thr Pro Ile Gln Ala Gly Gly Tyr Gly Ala Phe Pro Val His
        755                 760                 765

<210> SEQ ID NO 5
<211> LENGTH: 648
<212> TYPE: PRT
<213> ORGANISM: Homo sapiens

<400> SEQUENCE: 5

Met Glu His Ile Gln Gly Ala Trp Lys Thr Ile Ser Asn Gly Phe Gly
1               5                   10                  15
Phe Lys Asp Ala Val Phe Asp Gly Ser Ser Cys Ile Ser Pro Thr Ile
            20                  25                  30
Val Gln Gln Phe Gly Tyr Gln Arg Arg Ala Ser Asp Asp Gly Lys Leu
        35                  40                  45
Thr Asp Pro Ser Lys Thr Ser Asn Thr Ile Arg Val Phe Leu Pro Asn
    50                  55                  60
Lys Gln Arg Thr Val Val Asn Val Arg Asn Gly Met Ser Leu His Asp
65                  70                  75                  80
Cys Leu Met Lys Ala Leu Lys Val Arg Gly Leu Gln Pro Glu Cys Cys
                85                  90                  95
Ala Val Phe Arg Leu Leu His Glu His Lys Gly Lys Lys Ala Arg Leu
            100                 105                 110
Asp Trp Asn Thr Asp Ala Ala Ser Leu Ile Gly Glu Glu Leu Gln Val
        115                 120                 125
Asp Phe Leu Asp His Val Pro Leu Thr Thr His Asn Phe Ala Arg Lys
    130                 135                 140
Thr Phe Leu Lys Leu Ala Phe Cys Asp Ile Cys Gln Lys Phe Leu Leu
145                 150                 155                 160
Asn Gly Phe Arg Cys Gln Thr Cys Gly Tyr Lys Phe His Glu His Cys
                165                 170                 175
Ser Thr Lys Val Pro Thr Met Cys Val Asp Trp Ser Asn Ile Arg Gln
            180                 185                 190
Leu Leu Leu Phe Pro Asn Ser Thr Ile Gly Asp Ser Gly Val Pro Ala
        195                 200                 205
Leu Pro Ser Leu Thr Met Arg Arg Met Arg Glu Ser Val Ser Arg Met
    210                 215                 220
Pro Val Ser Ser Gln His Arg Tyr Ser Thr Pro His Ala Phe Thr Phe
225                 230                 235                 240
Asn Thr Ser Ser Pro Ser Ser Glu Gly Ser Leu Ser Gln Arg Gln Arg
                245                 250                 255
Ser Thr Ser Thr Pro Asn Val His Met Val Ser Thr Thr Leu Pro Val
            260                 265                 270
Asp Ser Arg Met Ile Glu Asp Ala Ile Arg Ser His Ser Glu Ser Ala
        275                 280                 285
Ser Pro Ser Ala Leu Ser Ser Ser Pro Asn Asn Leu Ser Pro Thr Gly
    290                 295                 300
Trp Ser Gln Pro Lys Thr Pro Val Pro Ala Gln Arg Glu Arg Ala Pro
305                 310                 315                 320
Val Ser Gly Thr Gln Glu Lys Asn Lys Ile Arg Pro Arg Gly Gln Arg
                325                 330                 335
```

Asp Ser Ser Tyr Tyr Trp Glu Ile Glu Ala Ser Glu Val Met Leu Ser
                340                 345                 350

Thr Arg Ile Gly Ser Gly Ser Phe Gly Thr Val Tyr Lys Gly Lys Trp
            355                 360                 365

His Gly Asp Val Ala Val Lys Ile Leu Lys Val Asp Pro Thr Pro
        370                 375                 380

Glu Gln Phe Gln Ala Phe Arg Asn Glu Val Ala Val Leu Arg Lys Thr
385                 390                 395                 400

Arg His Val Asn Ile Leu Leu Phe Met Gly Tyr Met Thr Lys Asp Asn
                405                 410                 415

Leu Ala Ile Val Thr Gln Trp Cys Glu Gly Ser Ser Leu Tyr Lys His
            420                 425                 430

Leu His Val Gln Glu Thr Lys Phe Gln Met Phe Gln Leu Ile Asp Ile
        435                 440                 445

Ala Arg Gln Thr Ala Gln Gly Met Asp Tyr Leu His Ala Lys Asn Ile
    450                 455                 460

Ile His Arg Asp Met Lys Ser Asn Asn Ile Phe Leu His Glu Gly Leu
465                 470                 475                 480

Thr Val Lys Ile Gly Asp Phe Gly Leu Ala Thr Val Lys Ser Arg Trp
                485                 490                 495

Ser Gly Ser Gln Gln Val Glu Gln Pro Thr Gly Ser Val Leu Trp Met
            500                 505                 510

Ala Pro Glu Val Ile Arg Met Gln Asp Asn Asn Pro Phe Ser Phe Gln
        515                 520                 525

Ser Asp Val Tyr Ser Tyr Gly Ile Val Leu Tyr Glu Leu Met Thr Gly
    530                 535                 540

Glu Leu Pro Tyr Ser His Ile Asn Asn Arg Asp Gln Ile Ile Phe Met
545                 550                 555                 560

Val Gly Arg Gly Tyr Ala Ser Pro Asp Leu Ser Lys Leu Tyr Lys Asn
                565                 570                 575

Cys Pro Lys Ala Met Lys Arg Leu Val Ala Asp Cys Val Lys Lys Val
            580                 585                 590

Lys Glu Glu Arg Pro Leu Phe Pro Gln Ile Leu Ser Ser Ile Glu Leu
        595                 600                 605

Leu Gln His Ser Leu Pro Lys Ile Asn Arg Ser Ala Ser Glu Pro Ser
    610                 615                 620

Leu His Arg Ala Ala His Thr Glu Asp Ile Asn Ala Cys Thr Leu Thr
625                 630                 635                 640

Thr Ser Pro Arg Leu Pro Val Phe
                645

<210> SEQ ID NO 6
<211> LENGTH: 648
<212> TYPE: PRT
<213> ORGANISM: Homo sapiens

<400> SEQUENCE: 6

Met Glu His Ile Gln Gly Ala Trp Lys Thr Ile Ser Asn Gly Phe Gly
1               5                   10                  15

Phe Lys Asp Ala Val Phe Asp Gly Ser Ser Cys Ile Ser Pro Thr Ile
                20                  25                  30

Val Gln Gln Phe Gly Tyr Gln Arg Arg Ala Ser Asp Asp Gly Lys Leu
            35                  40                  45

Thr Asp Pro Ser Lys Thr Ser Asn Thr Ile Arg Val Phe Leu Pro Asn

```
            50                  55                  60
Lys Gln Arg Thr Val Val Asn Val Arg Asn Gly Met Ser Leu His Asp
 65                  70                  75                  80

Cys Leu Met Lys Ala Leu Lys Val Arg Gly Leu Gln Pro Glu Cys Cys
                 85                  90                  95

Ala Val Phe Arg Leu Leu His Glu His Lys Gly Lys Lys Ala Arg Leu
                100                 105                 110

Asp Trp Asn Thr Asp Ala Ala Ser Leu Ile Gly Glu Glu Leu Gln Val
                115                 120                 125

Asp Phe Leu Asp His Val Pro Leu Thr Thr His Asn Phe Ala Arg Lys
            130                 135                 140

Thr Phe Leu Lys Leu Ala Phe Cys Asp Ile Cys Gln Lys Phe Leu Leu
145                 150                 155                 160

Asn Gly Phe Arg Cys Gln Thr Cys Gly Tyr Lys Phe His Glu His Cys
                165                 170                 175

Ser Thr Lys Val Pro Thr Met Cys Val Asp Trp Ser Asn Ile Arg Gln
                180                 185                 190

Leu Leu Leu Phe Pro Asn Ser Thr Ile Gly Asp Ser Gly Val Pro Ala
                195                 200                 205

Leu Pro Ser Leu Thr Met Arg Arg Met Arg Glu Ser Val Ser Arg Met
            210                 215                 220

Pro Val Ser Ser Gln His Arg Tyr Ser Thr Pro His Ala Phe Thr Phe
225                 230                 235                 240

Asn Thr Ser Ser Pro Ser Ser Glu Gly Ser Leu Ser Gln Arg Gln Arg
                245                 250                 255

Ser Thr Ser Thr Pro Asn Val His Met Val Ser Thr Thr Leu Pro Val
                260                 265                 270

Asp Ser Arg Met Ile Glu Asp Ala Ile Arg Ser His Ser Glu Ser Ala
            275                 280                 285

Ser Pro Ser Ala Leu Ser Ser Pro Asn Asn Leu Ser Pro Thr Gly
            290                 295                 300

Trp Ser Gln Pro Lys Thr Pro Val Pro Ala Gln Arg Glu Arg Ala Pro
305                 310                 315                 320

Val Ser Gly Thr Gln Glu Lys Asn Lys Ile Arg Pro Arg Gly Gln Arg
                325                 330                 335

Asp Ser Ser Tyr Tyr Trp Glu Ile Glu Ala Ser Glu Val Met Leu Ser
                340                 345                 350

Thr Arg Ile Gly Ser Gly Ser Phe Gly Thr Val Tyr Lys Gly Lys Trp
            355                 360                 365

His Gly Asp Val Phe Val Lys Ile Leu Lys Val Val Asp Pro Thr Pro
    370                 375                 380

Glu Gln Phe Gln Ala Phe Arg Asn Glu Val Ala Val Leu Arg Lys Thr
385                 390                 395                 400

Arg His Val Asn Ile Leu Leu Phe Met Gly Tyr Met Thr Lys Asp Asn
                405                 410                 415

Leu Ala Ile Val Thr Gln Trp Cys Glu Gly Ser Ser Leu Tyr Lys His
                420                 425                 430

Leu His Val Gln Glu Thr Lys Phe Gln Met Phe Gln Leu Ile Asp Ile
            435                 440                 445

Ala Arg Gln Thr Ala Gln Gly Met Asp Tyr Leu His Ala Lys Asn Ile
            450                 455                 460

Ile His Arg Asp Met Lys Ser Asn Asn Ile Phe Leu His Glu Gly Leu
465                 470                 475                 480
```

```
Thr Val Lys Ile Gly Asp Phe Gly Leu Ala Thr Val Lys Ser Arg Trp
            485                 490                 495
Ser Gly Ser Gln Val Glu Gln Pro Thr Gly Ser Val Leu Trp Met
            500                 505                 510
Ala Pro Glu Val Ile Arg Met Gln Asp Asn Asn Pro Phe Ser Phe Gln
            515                 520                 525
Ser Asp Val Tyr Ser Tyr Gly Ile Val Leu Tyr Glu Leu Met Thr Gly
            530                 535                 540
Glu Leu Pro Tyr Ser His Ile Asn Asn Arg Asp Gln Ile Ile Phe Met
545                 550                 555                 560
Val Gly Arg Gly Tyr Ala Ser Pro Asp Leu Ser Lys Leu Tyr Lys Asn
                565                 570                 575
Cys Pro Lys Ala Met Lys Arg Leu Val Ala Asp Cys Val Lys Lys Val
                580                 585                 590
Lys Glu Glu Arg Pro Leu Phe Pro Gln Ile Leu Ser Ser Ile Glu Leu
                595                 600                 605
Leu Gln His Ser Leu Pro Lys Ile Asn Arg Ser Ala Ser Glu Pro Ser
            610                 615                 620
Leu His Arg Ala Ala His Thr Glu Asp Ile Asn Ala Cys Thr Leu Thr
625                 630                 635                 640
Thr Ser Pro Arg Leu Pro Val Phe
                645

<210> SEQ ID NO 7
<211> LENGTH: 4553
<212> TYPE: DNA
<213> ORGANISM: Homo sapiens

<400> SEQUENCE: 7
ctggacccct gccagggaag gggtcctcag acttgaggtt gccagctcag atgtggggct      60
gctgatacta ggtgactgga ctgatgttct gttctagatg aaactccttg agggaccat     120 ttgaaaaggc ttgatgtgct gcccaaagcc cccttcagag ctgacttctc caccccagc     180 tgccgtgagc cttggctgct gacagctcat agctgagtcc ctcccgtgaa gtcaccttct     240
gctgaagggt acatcctctc ccaaggcgaa gctggtccgt tacatttgta agcagaggca     300
gtgcaagctg agcgtggctc ccggtgagag gaccccagag ctcaacagct acccccgctt     360
cagcgactgg ctgtacactt tcaacgtgag gccggaggtg gtgcaggaga tccccgaga     420 cctcacgctg gatgccctgc tggagatgaa tgaggccaag gtgaaggaga cgctgcggcg     480
ctgtggggcc agcggggatg agtgtggccg tctgcagtat gccctcacct gcctgcggaa     540
ggtgacaggc ctgggagggg agcacaagga ggactccagt tggagttcat tggatgcgcg     600
gcgggaaagt ggctcagggc cttccacgga caccctctca gcagccagcc tgccctggcc     660
cccagggagc tcccagctgg gcagagcagg caacagcgcc cagggcccac gctccatctc     720
cgtgtcagct ctgcccgcct cagactcccc cacccccagc ttcagtgagg cctctcaga     780 cacctgtatt ccctgcacg ccagcggccg gctgaccccc gtgccctgc acagcttcat     840 caccccgccc accacacccc agctgcgacg gcacaccaag ctgaagccac acgacgcc     900 ccccccaccc agccgcaagg tcttccagct gctgccagc ttccccacac tcacccggag     960
caagtcccat gagtctcagc tggggaaccg cattgatgac gtctcctcga tgaggtttga    1020
ttctctcgca tggatcccca cagatggtac ggagggatat cgggctgtcg gtgacgcaca    1080
ggttctccac caagtcctgg ctgtcgcagg tctgccacgt gtgccagaag agcatgatat    1140
```

```
ttggagtgaa gtgcaagcat tgcaggttga agtgtcacaa caaatgtacc aaagaagccc    1200
ctgcctgtag aatatccttc ctgccactaa ctcggcttcg gaggacagaa tctgtcccct    1260
cggacatcaa caacccggtg gacagagcag ccgaacccca ttttggaacc ctccccaaag    1320
cactgacaaa gaaggagcac cctccggcca tgaatcacct ggactccagc agcaaccctt    1380
cctccaccac ctcctccaca ccctcctcac cggcgccctt cccgacatca tccaacccat    1440
ccagcgccac cacgcccccc aacccctcac ctggccagcg ggacagcagg ttcaacttcc    1500
cagctgccta cttcattcat catagacagc agtttatctt tccagtgcca tctgctggcc    1560
attgctggaa atgcctcctt attgcagaaa gtttaaagga aaacgctttc aacatttcag    1620
cctttgcaca cgcagccccg ctccctgaag ctgccgacgg tacccggctc gatgaccagc    1680
cgaaagcaga tgtgttggaa gctcacgaag cggaggctga ggagccagag gctggcaagt    1740
cagaggcaga agacgatgag gacgaggtgg acgacttgcc gagctctcgc cggccctggc    1800
ggggccccat ctctcgcaag gccagccaga ccagcgtgta cctgcaggag tgggacatcc    1860
ccttcgagca ggtagagctg ggcgagccca tcgggcaggg ccgctggggc cgggtgcacc    1920
gcggccgctg gcatggcgag gtggccattc gcctgctgga gatggacggc cacaaccagg    1980
accacctgaa gctcttcaag aaagaggtga tgaactaccg gcagacgcgg catgagaacg    2040
tggtgctctt catggggggcc tgcatgaacc cgccccacct ggccattatc accagcttct    2100
gcaaggggcg gacgttgcac tcgtttgtga gggaccccaa gacgtctctg gacatcaaca    2160
agacgaggca aatcgctcag gagatcatca agggcatggg atatcttcat gccaagggca    2220
tcgtacacaa agatctcaaa tctaagaacg tcttctatga caacggcaag gtggtcatca    2280
cagacttcgg gctgtttggg atctcaggcg tggtccgaga gggacggcgt gagaaccagc    2340
taaagctgtc ccacgactgg ctgtgctatc tggcccctga gattgtacgc gagatgaccc    2400 ccggaagga cgaggatcag ctgccattct ccaaagctgc tgatgtctat gcatttggga    2460
ctgtttggta tgagctgcaa gcaagagact ggcсccttgaa gaaccaggct gcagaggcat    2520
ccatctggca gattggaagc ggggaaggaa tgaagcgtgt cctgacttct gtcagcttgg    2580
ggaaggaagt cagtgagatc ctgtcggcct gctgggcttt cgacctgcag agagacccca    2640
gcttcagcct gctgatggac atgctggaga acttcccaa gctgaaccgg cggctctccc    2700
accctggaca cttctggaag tcagctgagt tgtaggcctg gctgccttgc atgcaccagg    2760
ggctttcttc ctcctaatca acaactcagc accgtgactt ctgctaaaat gcaaaatgag    2820
atgcgggcac tacccagggg gatgccacct ctgctgctcc agtcgtctct ctcgaggcta    2880
cttcttttgc tttgttttaa aaactggccc tctgccctct ccacgtggcc tgcatatgcc    2940
caagtaactg ctctcagagg atcccactaa ctgcctccc tccaaggcag tctgggcagc    3000
ttctaactac cttcctggac atgactgatt gctcccgtgt tcttctgagg gctggtcttg    3060

tttttgttt ggtggctctg tctcactgct aacaccttag tgagatgcct tccaccctcc    3120
tgagcacacc agcctcccac tgggtgtgtg cctagtgcgg ggcgggcgga ggttgggagg    3180
gtgttggctt ggcttttaac ctgtgggat tttgtccaac aaggagtgga atgatttcag    3240
agctgccctg aggctggcac cctggtcaca ggaaccctct cgcgctggct ctgtctcagt    3300

cccctctgta gagttagatc agaagacaca gaaagttctg tggccatgaa agataccagc    3360
ttggaagggt tgtgtcttca gtggcaccct cagaaaaatt gtcttaaagc aaagaggtac    3420
ctggctccag acaatttttc tgatgaaaac aaagtctctg ccccgtcccc accctgccac    3480
```

```
cctggcaaag ttacttcctt tacagctgcc cagtgtacca tagaccagac cccaggtcag   3540
catttgtcaa gagcatggct gctgagtccc ctgtggcagt caatgcactg tttaccaaat   3600
gcaggtttct gttctccctc cccagcaaga cctgctgaac ccagatctct ggaatggggc   3660
cctaggaatt tgcatttcaa cctgcttccc aggtggccct gatgcacccc agtattagag   3720
tttattgcta aaaggaacat gccctgtcac tcctggtatc ctgggagtca tgtttctctt   3780
ctctctcagt tctacttgga gcaagagctt tcctgggctg caaatgagaa acaattcct   3840 aggaacccac agcagtactg agcatgctgg gagcttggga cttggagatg aatgagccac   3900
cgttgctgct ccaagtagga ctacttggag tgtagctgag gccttggacg cagtatgacc   3960
aggggcagct ctgccagggc tgttggccaa tcagtcattt tcatttcttg ttggaggcca   4020
ggtcctctgc tgaactcatt tcctagctag tgttaccta attctgatga agatcaatgg   4080
ggctataatt cttgttttg ttcctctttg cagcattaac agcagcaaag ttgtaccccg   4140
gtttgaaagg tttggcttgg gcgtcctgga gtccagtaat ccaaagatgt agccagccat   4200 atggttttc gctgctgatc tctttctttt taaaatgtgt ttctgaaaca tcccaacaac   4260
caccacgaca aaaaacact gcctgccag cgctgcaaac caggagcaca cgtcctagat   4320
tcagactgtt ggccataaac cccactcggg agatggagct gcacctgcta tttcttaaaa   4380
tgacaccacc aacaaccaaa cctgtcatga cagacagcaa atgtttacac gtatatttct   4440
cctgagtgaa cctgatgttt tacaataggt aataataaaa acagtctgtg caaaaaaaaa   4500 aaaaaaaaa aaaaaaaaa aaaaaaaaa aaaaaaaaa aaaaaaaaa aaa              4553

<210> SEQ ID NO 8
<211> LENGTH: 762
<212> TYPE: PRT
<213> ORGANISM: Homo sapiens

<400> SEQUENCE: 8

Met Asn Glu Ala Lys Val Lys Glu Thr Leu Arg Arg Cys Gly Ala Ser
1               5                   10                  15

Gly Asp Glu Cys Gly Arg Leu Gln Tyr Ala Leu Thr Cys Leu Arg Lys
            20                  25                  30

Val Thr Gly Leu Gly Gly Glu His Lys Glu Asp Ser Ser Trp Ser Ser
        35                  40                  45

Leu Asp Ala Arg Arg Glu Ser Gly Ser Gly Pro Ser Thr Asp Thr Leu
    50                  55                  60

Ser Ala Ala Ser Leu Pro Trp Pro Pro Gly Ser Ser Gln Leu Gly Arg
65                  70                  75                  80

Ala Gly Asn Ser Ala Gln Gly Pro Arg Ser Ile Ser Val Ser Ala Leu
                85                  90                  95

Pro Ala Ser Asp Ser Pro Thr Pro Ser Phe Ser Glu Gly Leu Ser Asp
            100                 105                 110

Thr Cys Ile Pro Leu His Ala Ser Gly Arg Leu Thr Pro Arg Ala Leu
        115                 120                 125

His Ser Phe Ile Thr Pro Pro Thr Pro Gln Leu Arg Arg His Thr
    130                 135                 140

Lys Leu Lys Pro Pro Arg Thr Pro Pro Pro Ser Arg Lys Val Phe
145                 150                 155                 160

Gln Leu Leu Pro Ser Phe Pro Thr Leu Thr Arg Ser Lys Ser His Glu
                165                 170                 175

Ser Gln Leu Gly Asn Arg Ile Asp Asp Val Ser Ser Met Arg Phe Asp
            180                 185                 190
```

Leu Ser His Gly Ser Pro Gln Met Val Arg Arg Asp Ile Gly Leu Ser
        195                 200                 205

Val Thr His Arg Phe Ser Thr Lys Ser Trp Leu Ser Gln Val Cys His
        210                 215                 220

Val Cys Gln Lys Ser Met Ile Phe Gly Val Lys Cys Lys His Cys Arg
225                 230                 235                 240

Leu Lys Cys His Asn Lys Cys Thr Lys Glu Ala Pro Ala Cys Arg Ile
                245                 250                 255

Ser Phe Leu Pro Leu Thr Arg Leu Arg Arg Thr Glu Ser Val Pro Ser
                260                 265                 270

Asp Ile Asn Asn Pro Val Asp Arg Ala Ala Glu Pro His Phe Gly Thr
                275                 280                 285

Leu Pro Lys Ala Leu Thr Lys Lys Glu His Pro Pro Ala Met Asn His
        290                 295                 300

Leu Asp Ser Ser Ser Asn Pro Ser Ser Thr Thr Ser Ser Thr Pro Ser
305                 310                 315                 320

Ser Pro Ala Pro Phe Pro Thr Ser Ser Asn Pro Ser Ser Ala Thr Thr
                325                 330                 335

Pro Pro Asn Pro Ser Pro Gly Gln Arg Asp Ser Arg Phe Asn Phe Pro
        340                 345                 350

Ala Ala Tyr Phe Ile His His Arg Gln Gln Phe Ile Phe Pro Val Pro
            355                 360                 365

Ser Ala Gly His Cys Trp Lys Cys Leu Leu Ile Ala Glu Ser Leu Lys
        370                 375                 380

Glu Asn Ala Phe Asn Ile Ser Ala Phe Ala His Ala Ala Pro Leu Pro
385                 390                 395                 400

Glu Ala Ala Asp Gly Thr Arg Leu Asp Asp Gln Pro Lys Ala Asp Val
                405                 410                 415

Leu Glu Ala His Glu Ala Glu Ala Glu Pro Glu Ala Gly Lys Ser
                420                 425                 430

Glu Ala Glu Asp Asp Glu Asp Glu Val Asp Asp Leu Pro Ser Ser Arg
        435                 440                 445

Arg Pro Trp Arg Gly Pro Ile Ser Arg Lys Ala Ser Gln Thr Ser Val
        450                 455                 460

Tyr Leu Gln Glu Trp Asp Ile Pro Phe Glu Gln Val Glu Leu Gly Glu
465                 470                 475                 480

Pro Ile Gly Gln Gly Arg Trp Gly Arg Val His Arg Gly Arg Trp His
                485                 490                 495

Gly Glu Val Ala Ile Arg Leu Phe Glu Met Asp Gly His Asn Gln Asp
                500                 505                 510

His Leu Lys Leu Phe Lys Lys Glu Val Met Asn Tyr Arg Gln Thr Arg
        515                 520                 525

His Glu Asn Val Val Leu Phe Met Gly Ala Cys Met Asn Pro Pro His
        530                 535                 540

Leu Ala Ile Ile Thr Ser Phe Cys Lys Gly Arg Thr Leu His Ser Phe
545                 550                 555                 560

Val Arg Asp Pro Lys Thr Ser Leu Asp Ile Asn Lys Thr Arg Gln Ile
                565                 570                 575

Ala Gln Glu Ile Ile Lys Gly Met Gly Tyr Leu His Ala Lys Gly Ile
            580                 585                 590

Val His Lys Asp Leu Lys Ser Lys Asn Val Phe Tyr Asp Asn Gly Lys
        595                 600                 605

-continued

```
Val Val Ile Thr Asp Phe Gly Leu Phe Gly Ile Ser Gly Val Val Arg
    610             615             620
Glu Gly Arg Arg Glu Asn Gln Leu Lys Leu Ser His Asp Trp Leu Cys
625             630              635             640
Tyr Leu Ala Pro Glu Ile Val Arg Glu Met Thr Pro Gly Lys Asp Glu
            645             650             655
Asp Gln Leu Pro Phe Ser Lys Ala Ala Asp Val Tyr Ala Phe Gly Thr
            660             665             670
Val Trp Tyr Glu Leu Gln Ala Arg Asp Trp Pro Leu Lys Asn Gln Ala
        675             680             685
Ala Glu Ala Ser Ile Trp Gln Ile Gly Ser Gly Glu Gly Met Lys Arg
690             695             700
Val Leu Thr Ser Val Ser Leu Gly Lys Glu Val Ser Glu Ile Leu Ser
705             710             715             720
Ala Cys Trp Ala Phe Asp Leu Gln Glu Arg Pro Ser Phe Ser Leu Leu
            725             730             735
Met Asp Met Leu Glu Lys Leu Pro Lys Leu Asn Arg Arg Leu Ser His
            740             745             750
Pro Gly His Phe Trp Lys Ser Ala Glu Leu
        755             760

<210> SEQ ID NO 9
<211> LENGTH: 20
<212> TYPE: PRT
<213> ORGANISM: Homo sapiens

<400> SEQUENCE: 9

Met Lys Thr Leu Gly Arg Arg Asp Asp Asp Asp Trp Glu Ile Pro
1               5               10              15
Asp Gly Gly Ile
            20

<210> SEQ ID NO 10
<211> LENGTH: 19
<212> TYPE: PRT
<213> ORGANISM: Homo sapiens

<400> SEQUENCE: 10

Met Lys Thr Leu Gly Arg Arg Asp Ser Ser Asp Asp Trp Glu Ile Pro
1               5               10              15
Asp Gly Gln
```